United States Patent
Biser

(10) Patent No.: US 8,636,786 B2
(45) Date of Patent: Jan. 28, 2014

(54) THERMAL COMPRESS SYSTEM AND METHODS OF USING THE SAME

(76) Inventor: Seth A. Biser, Fleetwood, NY (US)

(*) Notice: Subject to any disclaimer, the term of this patent is extended or adjusted under 35 U.S.C. 154(b) by 46 days.

(21) Appl. No.: 12/947,189

(22) Filed: Nov. 16, 2010

(65) Prior Publication Data

US 2011/0178585 A1    Jul. 21, 2011

Related U.S. Application Data

(63) Continuation of application No. PCT/US2009/044327, filed on May 18, 2009, which is a continuation-in-part of application No. 12/153,322, filed on May 16, 2008, and a continuation-in-part of application No. 12/153,321, filed on May 16, 2008.

(51) Int. Cl.
    *A61F 7/00*  (2006.01)
(52) U.S. Cl.
    USPC ............................................... 607/107
(58) Field of Classification Search
    USPC ........ 607/108–112, 114; 2/173, 426–454, 15; D2/880–881; D24/206–208
    See application file for complete search history.

(56) References Cited

U.S. PATENT DOCUMENTS

| | | |
|---|---|---|
| 702,759 A | 6/1902 | Allegretti |
| 1,161,321 A | 11/1915 | Lush |
| 1,275,127 A | 8/1918 | Campbell |
| 1,567,931 A | 12/1925 | Epler |
| 1,743,244 A | 1/1930 | Shulman |
| 1,799,064 A | 3/1931 | Rickerd |
| 1,886,725 A | 11/1932 | Pederson |
| 2,101,628 A | 12/1937 | Padelford |
| 2,237,971 A | 4/1941 | Padelford |
| 2,342,840 A | 2/1944 | Cadous |
| 2,343,157 A | 2/1944 | Quering |
| 2,586,851 A | 2/1952 | Monro et al. |
| 2,755,803 A | 7/1956 | Dorsey |
| 2,796,903 A * | 6/1957 | Gazelle .................. 607/109 |

(Continued)

FOREIGN PATENT DOCUMENTS

| | | |
|---|---|---|
| CN | 101172183 | 11/2006 |
| JP | S63-62119 | 4/1988 |

(Continued)

OTHER PUBLICATIONS

International Search Report and Written Opinion for PCT Application No. PCT/US2009/044327, mailed Jul. 16, 2009, 9 pgs.

(Continued)

*Primary Examiner* — Linda Dvorak
*Assistant Examiner* — Adam Avigan
(74) *Attorney, Agent, or Firm* — Cooley LLP

(57) ABSTRACT

An eye compress kit includes a thermally adjustable gel pack, a strap and at least one moistened, disposable fibrous non-woven fabric sheet. The thermally adjustable gel pack is configured to be applied against an eye region of a user's body. The gel pack includes a casing that defines a chamber holding a thermally activatable gelatinous substance. The strap is configured to secure the gel pack against the user's eye region and to exert compressive forces to the gel pack. The at least one moistened, disposable fibrous non-woven fabric sheet is adapted to be positioned between the gel pack and the user's eye region wherein the fabric sheet is removable from the outer surface of the gel pack.

21 Claims, 19 Drawing Sheets

(56) References Cited

U.S. PATENT DOCUMENTS

| | | | |
|---|---|---|---|
| 3,173,419 A * | 3/1965 | Dubilier et al. | 607/109 |
| 3,333,586 A | 8/1967 | Bellis et al. | |
| 3,768,485 A | 10/1973 | Linick | |
| 3,804,077 A | 4/1974 | Williams | |
| 3,836,044 A | 9/1974 | Tilp et al. | |
| 3,885,403 A | 5/1975 | Spencer | |
| 4,019,516 A | 4/1977 | D'Auria | |
| 4,190,054 A | 2/1980 | Brennan | |
| 4,243,041 A | 1/1981 | Paul | |
| 4,252,119 A | 2/1981 | Coates | |
| 4,261,364 A | 4/1981 | Haddad et al. | |
| 4,372,318 A | 2/1983 | Viesturs et al. | |
| 4,473,370 A | 9/1984 | Weiss | |
| 4,517,972 A | 5/1985 | Finch, Jr. | |
| 4,527,565 A | 7/1985 | Ellis | |
| 4,614,189 A * | 9/1986 | MacKenzie | 607/109 |
| 4,671,267 A | 6/1987 | Stout | |
| 4,676,247 A | 6/1987 | Van Cleve | |
| 4,756,311 A * | 7/1988 | Francis, Jr. | 607/114 |
| 4,783,866 A | 11/1988 | Simmons et al. | |
| 4,856,651 A | 8/1989 | Francis, Jr. | |
| 4,910,978 A | 3/1990 | Gordon et al. | |
| 5,016,629 A | 5/1991 | Kanare | |
| 5,035,241 A | 7/1991 | Walasek et al. | |
| 5,065,758 A | 11/1991 | Whitehead et al. | |
| 5,069,208 A | 12/1991 | Noppel et al. | |
| 5,094,238 A | 3/1992 | Gibbon | |
| 5,119,812 A | 6/1992 | Angelo | |
| 5,129,391 A | 7/1992 | Brodsky et al. | |
| 5,188,103 A | 2/1993 | Smith | |
| 5,190,032 A | 3/1993 | Zacoi | |
| 5,190,033 A | 3/1993 | Johnson | |
| 5,274,865 A | 1/1994 | Takehashi | |
| 5,314,456 A | 5/1994 | Cohen | |
| 5,392,945 A | 2/1995 | Syrek | |
| 5,409,500 A | 4/1995 | Dyrek | |
| 5,456,703 A | 10/1995 | Beeuwkes, III | |
| 5,458,628 A | 10/1995 | Cipolla | |
| 5,545,197 A | 8/1996 | Bowen | |
| 5,628,772 A * | 5/1997 | Russell | 607/109 |
| 5,643,336 A | 7/1997 | Lopez-Ciaros | |
| 5,679,052 A | 10/1997 | Rucki | |
| 5,700,238 A | 12/1997 | Hyson | |
| 5,716,388 A | 2/1998 | Petelle | |
| 5,733,321 A | 3/1998 | Brink | |
| 5,837,004 A | 11/1998 | Lavore | |
| 5,840,080 A | 11/1998 | Der Ovanesian | |
| 5,879,379 A | 3/1999 | Mason et al. | |
| 5,980,497 A | 11/1999 | Yavitz | |
| 6,017,606 A | 1/2000 | Sage et al. | |
| 6,030,412 A | 2/2000 | Klatz et al. | |
| 6,083,254 A | 7/2000 | Evans | |
| 6,083,256 A * | 7/2000 | Der Ovanesian | 607/114 |
| D432,658 S | 10/2000 | Haynes | |
| 6,126,683 A | 10/2000 | Momtaheni | |
| 6,129,659 A | 10/2000 | Wilk | |
| 6,138,286 A | 10/2000 | Robrahn et al. | |
| 6,155,995 A | 12/2000 | Lin | |
| 6,193,740 B1 | 2/2001 | Rodriguez | |
| 6,241,711 B1 | 6/2001 | Weissberg et al. | |
| 6,248,125 B1 | 6/2001 | Helming | |
| D446,863 S | 8/2001 | Carroll | |
| 6,312,125 B1 | 11/2001 | Potts | |
| 6,316,687 B1 | 11/2001 | Davis et al. | |
| 6,409,746 B1 | 6/2002 | Igaki et al. | |
| 6,451,046 B1 | 9/2002 | Leo et al. | |
| D464,140 S | 10/2002 | Lavin, Jr. | |
| 6,514,279 B1 | 2/2003 | Lavin | |
| 6,537,308 B2 | 3/2003 | Burkhart | |
| 6,571,799 B1 | 6/2003 | Daly | |
| 6,589,272 B1 | 7/2003 | Sheikh | |
| 6,623,517 B1 | 9/2003 | DeLuisa et al. | |
| 6,648,909 B2 | 11/2003 | Helming | |
| 6,656,210 B1 | 12/2003 | Plewes | |
| 6,823,860 B2 | 11/2004 | Igaki et al. | |
| 6,824,556 B1 | 11/2004 | Lachance | |
| 6,886,553 B2 | 5/2005 | Yim | |
| 6,886,933 B2 | 5/2005 | Schwebel | |
| 6,908,195 B2 | 6/2005 | Fuller | |
| 6,931,664 B1 * | 8/2005 | Chen | 2/9 |
| 6,936,018 B2 | 8/2005 | Chalek | |
| 7,211,070 B2 | 5/2007 | Soroudi | |
| 7,231,922 B2 | 6/2007 | Davison et al. | |
| 7,243,509 B2 | 7/2007 | Trinh et al. | |
| 7,264,630 B1 | 9/2007 | Webb | |
| 7,395,554 B2 | 7/2008 | Kitayama | |
| 8,333,793 B2 * | 12/2012 | Igaki et al. | 607/109 |
| 2001/0039442 A1 * | 11/2001 | Gorge et al. | 607/109 |
| 2004/0138729 A1 | 7/2004 | Ladmer | |
| 2005/0187502 A1 | 8/2005 | Krempel et al. | |
| 2005/0229281 A1 * | 10/2005 | Glasser | 2/15 |
| 2005/0278008 A1 | 12/2005 | Ladmer | |
| 2006/0058840 A1 | 3/2006 | Payne | |
| 2006/0157064 A1 | 7/2006 | Davison et al. | |
| 2006/0210616 A1 | 9/2006 | Linder | |
| 2007/0016254 A1 | 1/2007 | Grenon et al. | |
| 2007/0016256 A1 | 1/2007 | Korb et al. | |
| 2007/0022521 A1 * | 2/2007 | Seynhaeve et al. | 2/426 |
| 2007/0027431 A1 | 2/2007 | Korb et al. | |
| 2007/0049913 A1 | 3/2007 | Grenon et al. | |
| 2007/0060988 A1 | 3/2007 | Grenon et al. | |
| 2008/0114422 A1 | 5/2008 | Korb et al. | |
| 2008/0114423 A1 | 5/2008 | Grenon et al. | |
| 2008/0114425 A1 | 5/2008 | Korb et al. | |
| 2008/0114426 A1 | 5/2008 | Korb et al. | |
| 2009/0287282 A1 | 11/2009 | Biser et al. | |
| 2009/0287283 A1 | 11/2009 | Biser et al. | |

FOREIGN PATENT DOCUMENTS

| | | |
|---|---|---|
| JP | H10-211228 | 8/1998 |
| JP | 2000-116430 | 4/2000 |
| JP | 2004-350803 | 12/2004 |
| WO | WO 01/39704 | 6/2001 |
| WO | WO 2009/140673 | 11/2009 |

OTHER PUBLICATIONS

The Dry Eye Zone, "Warm Compresses"[online], [initially retrieved on Feb. 1, 2008]. Retrieved from the Internet: <URL: http://www.dryeyezone.com/encyclopedia/hotcompresses.html> (2 pgs).

Make Me Heal "Cold & Hot Eye Compress (w/cheek and temple coverage)" [online], [initially retrieved on Feb. 1, 2008]. Retrieved from the Internet <URL: http://www.makemeheal.com/mmh/product.do;jsessionid=87AE399BAA6CD81AD88A660B0191417C?id=10001&procid=10&catid=30> (3 pgs).

Ophthalmology Management "Enhancing Dry Eye Therapy" [online], Retrieved from the Internet <URL: http://www.ophmanagement.com/article.aspx?article=85198>, published Sep. 2001 (3 pgs).

Corso Enterprises, Inc. "Eyes Pack" [online], [initially retrieved on Jan. 21, 2008] Retrieved from the Internet <URL: http://www.eyespack.com/eyespack.html> (6 pgs).

Dry Eye Talk "Suggestions on Hot Compress while away from home." [online], Post #7 by Rebecca Petris, Administrator, on Apr. 10, 2006, Retrieved from the Internet <URL: http://www.dryeyezone.com/talk/showthread.php?t=1254> (2 pgs).

Eye World News Magazine "Reporting Live from New Orleans AAO 2004" Scheffer C.G. Tseng, M.D., Ph.D., "Warming device relieves post-LASIK dry eye, research says" (p. 1) [online], Retrieved from the Internet <URL: http://www.eyeworld.org/article.php?sid=2248&strict=&morphologic=&query=slt> (10 pgs).

Dry Eye Talk "thermoeyes" [online], Post #1 By Rebecca Petris, Administrator, on May 3, 2006, Retrieved from the Internet <URL: http://www.dryeyezone.com/talk/showthread.php?t=1339> (2 pgs).

Moist Heat Therapy Warming Eye Pillow by Spa Necessities, [Online] Retrieved from the Internet: <URL: http://www.amazon.com/Moist-Heat-Therapy-Warming-Pillow/dp/B0000ZH3F0?SubscriptionId=1GKMRWT8RXFTWF55P882&tag=lightingelect-20&linkCode=xm2&camp=2025&creative=165953&creativeASIN=B0000ZH3F0> Dec. 8, 2011 (6 pages).

(56) References Cited

OTHER PUBLICATIONS

Brookstone Hot/Cold Antistress Sinus Mask Reviews, [Online] Retrieved from the Internet: <URL: http://www.buzzillions.com/reviews/brookstone-hot-cold-anti-stress-sinus-mask-reviews> Dec. 8, 2011 (4 pages).

Brookstone Hot/Cold Anti Stress Sinus Mask Description, [Online] Retrieved from the Internet: <URL: http://www.buzzillions.com/reviews/brookstone-hot-cold-anti-stress-sinus-mask-reviews#Description> Dec. 8, 2011 (1 page).

Thermalon Dry Eye Compress, [Online] Retrieved from the internet: <URL: http://www.amazon.com/Thermalon-24342-Dry-Eye-Compress/dp/B004385RPS/ref=sr_1_1?s=hpc&ie=UTF8&qid=1321925614&sr=1-1> Dec. 8, 2011 (7 pages).

Elasto Gel Hot/Cold Sinus Mask, [Online] Retrieved from the Internet: <URL: http://www.amazon.com/Elasto-Hot-Cold-Sinus-Mask/dp/B000FHZNQE/ref=pd_sim_hpc_5> Dec. 8, 2011 (8 pages).

The Body Shop Eye Gel Mask, [Online] Retrieved from the Internet: <URL: http://www.totalbeauty.com/reviews/product/6096441/the-body-shop-eye-gel-mask> Dec. 8, 2011 (2 pages).

Taiwan Stanch Product—Beauty Series, [Online] Retrieved from the Internet: <URL: http://www.taiwanstanch.com/product_explanationE.asp?kind=90&id=185&Page=1> Dec. 8, 2011 (1 page).

Gel Eye Mask (VS-TRM01), [Online] Retrieved from the Internet: <URL: http://hzvison.en.made-in-china.com/product/weEQGmfeqkhH/China-Gel-Eye-Mask-VS-TRM01-html> Dec. 8, 2011 (1 page).

Eye Mask, Information about the Eye Comfort Gel Pack, [Online] Retrieved from the Internet: <URL: http://www.accurategelpacks.com/eye_mask.html> Dec. 8, 2011 (1 page).

OCuSOFT Lid Scrub Original Pre-Moistened Pads (30/Ctn), [Online] Retrieved from the Internet: <URL:http://www.ocusoft.com/730-1-90.html> Dec. 8, 2011 (1 page).

"Eyes Pack", Eyes Pack Bilateral Eye Compress; Item# CE-101 Red/CE-102 Green; Corso Enterprises, Inc.; pp. 1-6; httg://www.eyespack.corn/eyespack.html.

Office Action mailed Jun. 9, 2011 for U.S. Appl. No. 12/153,322, filed May 16, 2008.

Office Action mailed Sep. 12, 2012, for U.S. Appl. No. 12/153,322, filed May 16, 2008.

Final Office Action mailed Mar. 14, 2012 for U.S. Appl. No. 12/153,322, filed May 16, 2008.

Office Action mailed Jun. 9, 2011 for U.S. Appl. No. 12/153,321, filed May 16, 2008.

Final Office Action mailed Aug. 29, 2012 for U.S. Appl. No. 12/153,321, filed May 16, 2008.

Final Office Action mailed Jun. 12, 2012 for U.S. Appl. No. 12/153,321, filed May 16, 2008.

Office Action dated Jul. 2, 2012 for Chinese Application No. 2009801208470.

Office Action dated Mar. 28, 2013 for Chinese Application No. 2009801208470.

Office Action dated Jan. 4, 2013 for European Application No. EP 09 74 7754.

Office Action dated May 28, 2013 for Japanese Application No. 2011-509789.

Office Action mailed Jul. 8, 2013 for U.S. Appl. No. 12/153,322.

* cited by examiner

THERMAL COMPRESS SYSTEM AND METHODS OF USING THE SAME

CROSS-REFERENCE TO RELATED APPLICATIONS

This application claims priority to and is a continuation of PCT Patent Application Serial No. PCT/US2009/044327, filed May 18, 2009 entitled "Thermal Compress System and Methods of Using the Same", which is a continuation-in-part of U.S. patent application Ser. No. 12/153,322, filed May 16, 2008 entitled "Thermal Compress Assembly and System with External Frame", and U.S. patent application Ser. No. 12/153,321, filed May 16, 2008 entitled "Thermal Bodily Compress Kits and Methods of Using Same", each of which is incorporated herein by reference in its entirety.

TECHNICAL FIELD

The invention is directed to, for example, thermal body compress devices, kits, assemblies, systems, and methods of using the same to provide therapeutic benefit to a user's eye region.

BACKGROUND

Both hot and cold compresses play an important role in treating various physical problems. In the most common and traditional method of compress therapy, the user holds a washcloth either under hot or cold running tap water, or in a basin of hot or cold water, and then applies the moist, temperature-adjusted washcloth to the body part. This method is popular because washcloths are low in cost and widely available, they are reasonably soft in texture, and their temperature can usually be determined by the user. In addition, the washcloth method allows the user to select how the external pressure is applied against the body part. The specific case of eye compresses is illustrative. Because the eyes are one of the most sensitive and delicate of bodily tissues, most users of the washcloth method will avoid putting pressure directly on the round globe of the eye (the eyeball), and will instead press the washcloth gently into other areas such as the corners of the eyes. The washcloth thereby passively conforms to the round globe of the eye in a safe and comfortable way. Additionally, a wet washcloth provides a moist thermal treatment. Therefore, the washcloth method has been viewed as being particularly useful for hot compress therapy.

However, the washcloth method has numerous disadvantages. The washcloth's temperature decays relatively quickly necessitating frequent re-heatings or re-coolings, especially if the washcloth is wrung out after immersion in water. In the case of compress therapy applied to the eyes or other specific head regions, the washcloth may drape uncomfortably over the face and, if too wet, will tend to drip down the user's arm as the user stands at the sink. Repeated use on a body part of a washcloth left in a bathroom, especially when the bathroom is shared by more than one person, may be unhygienic.

Other efforts to apply sustained thermal application as a part of compress therapy are also known. One example is a gel pack, which can be heated and applied against a user's body.

Known gel packs designed specifically for use on the eyes and periorbital regions have been manufactured with casings made of PVC or vinyl materials, which have the benefit of low production costs. However, such casing materials have various characteristics that limit their effectiveness for ocular thermal therapy.

Further, known gel packs fail to provide a convenient presence of moisture in order to produce an effective moist thermal treatment. Additionally, known gel packs fail to provide various chemical agents to the skin to support the health of the skin during repeated treatments of thermal compress therapy. Known gel packs also fail to provide an adjustable degree of compression against the gel pack that allows the user to select how the external pressure is applied against the body part as well as how much external pressure is applied to the body part.

Accordingly, a need exists for various components of a thermally and mechanically adjustable compress system which will impart comfortable and effective therapy to sensitive body parts, such as the ocular region, in a safe and convenient manner.

SUMMARY

An eye compress kit includes a thermally adjustable gel pack, a strap and at least one moistened, disposable fibrous non-woven fabric sheet. The thermally adjustable gel pack is configured to be applied against an eye region of a user's body. The gel pack includes a casing that defines a chamber holding a thermally activatable gelatinous substance. The strap is configured to secure the gel pack against the user's eye region and to exert compressive forces to the gel pack. The at least one moistened, disposable fibrous non-woven fabric sheet is adapted to be positioned between the gel pack and the user's eye region wherein the fabric sheet is removable from the outer surface of the gel pack.

DETAILED DESCRIPTION

The invention is directed to, for example, thermally adjustable body compress devices, assemblies, kits, systems, and methods of preparing and using the same. The devices and methods can be used to treat or alleviate a variety of abnormal physiological conditions in users or to provide therapeutic benefit to users who are otherwise in normal condition. The devices and methods can be applied to various body parts such as, for example, the soft tissues, muscles, bones, and other tissues and organs of a user. Although embodiments will be described with relation to applying the compress devices and methods to an eye region of a user, it is understood that other embodiments have broader application to other parts of the anatomy. As used herein, the term "user" includes mammalian subjects including humans.

In some embodiments, an eye region of a user that is treated by devices and methods described herein includes the periocular region. The periocular region is defined as including the eyelid, including the skin of the upper and lower eyelids; the eyelid margins; and the lateral canthus and the medial canthus. In other embodiments, the eye region includes the periorbital region. The periorbital region is defined as including the lower brow region, the upper cheek region, the bridge of the nose, and at least a portion of the temple of the head. In other embodiments, the eye region includes both the periocular region and the periorbital region. The above described anatomical sites are described in the singular tense but it is understood that these regions are bilateral and thus embodiments can also cover both the left and right periocular and/or periorbital regions. In some embodiments, the eye region includes the entire temple(s) of the head.

Figure 1:
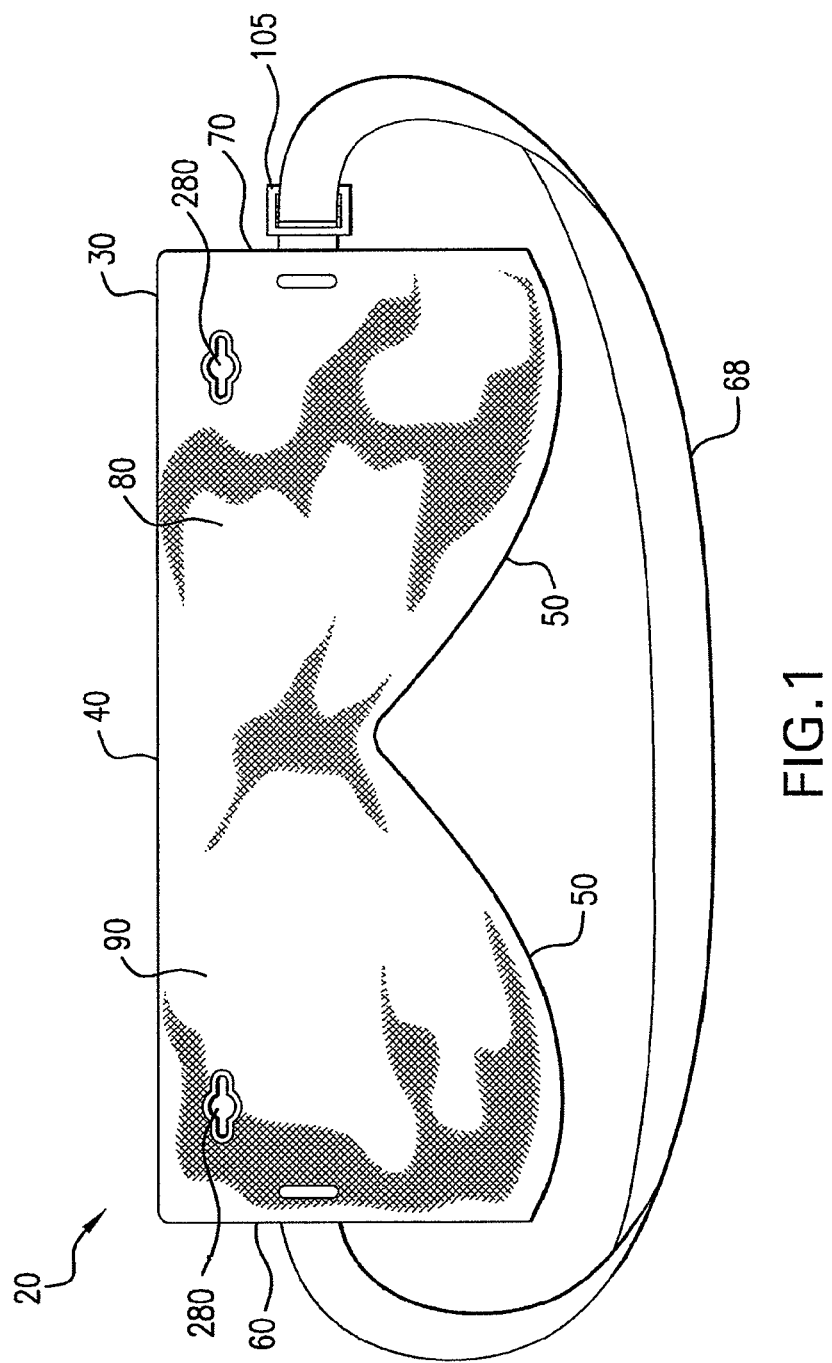
FIG. 1 is a perspective view of a gel pack according to an embodiment.

FIG. 1, shows a compress assembly and system having a thermally adjustable pack 20 configured to be applied against the eye region of a user's face to apply a sufficient heat or cold source to the user's eye region to provide a therapeutic benefit to the user. Accordingly, pack 20 comprises a thermally activatable substance whose temperature can be regulated or adjusted by applying various degrees of heat or cold. Such a substance is capable, at a minimum, of being warmed or cooled so that it achieves a temperature that is substantially different from room temperature, and sustains the achieved temperature for a relatively long period of time and with a relatively slow period of decline back toward room temperature. In some embodiments, for example, 2.5 ounces of such a substance can be heated to 135° F. and will still have a temperature of at least 115° F. after 5 minutes of exposure to 72° F. air. Non-limiting examples of thermally activatable substances include water; various gelatinous materials such as solid or semi-solid gels, including solutions containing sodium acetate trihydrate, which can be chemically activated with a nucleation center or other means to produce an exothermic reaction; dried vegetables and cereals such as rice, beans, corn, and peas; water-containing food products such as potatoes and apples; and various other vegetables and food products. In some embodiments, the thermally activatable substance is a gelatinous substance (also referred to herein as a "gel" or "gelatinous material") and the thermally activatable pack is a gel pack. The below-described embodiments will be described with respect to a gelatinous substance although it is understood that other thermally activatable substances can also be used.

Referring again to FIG. 1, gel pack 20 includes a casing 30 having a top portion 40, a bottom portion 50, a right portion 60, a left portion 70, a front side and a back side. As used herein in relation to the below description and accompanying figures, the terms "top," "bottom," "left," "right," "front," and "back" refer to the orientation of the gel pack and compress assembly in relation to the user, in an applied position on the user's face when the user is standing upright (a position known in the art as the "anatomical position") and facing out of the page toward the viewer. The gel pack and compress assembly can be used either in an upright (sitting or standing) or recumbent position. The front side of the gel pack is the side that faces outwardly and is the side illustrated in FIG. 1. The back side is the opposite side of the gel pack which faces the user in an applied position of the gel pack (i.e. when the gel pack is in use). Gel pack 20 defines a chamber 80 (illustrated more clearly in FIG. 2) holding a gelatinous thermal substance 90. In some embodiments, the gel pack has a substantially uniform thickness between about 0.25 inches and 0.35 inches when in a resting position (i.e., the gel is substantially evenly distributed throughout the gel pack).

Figure 2:
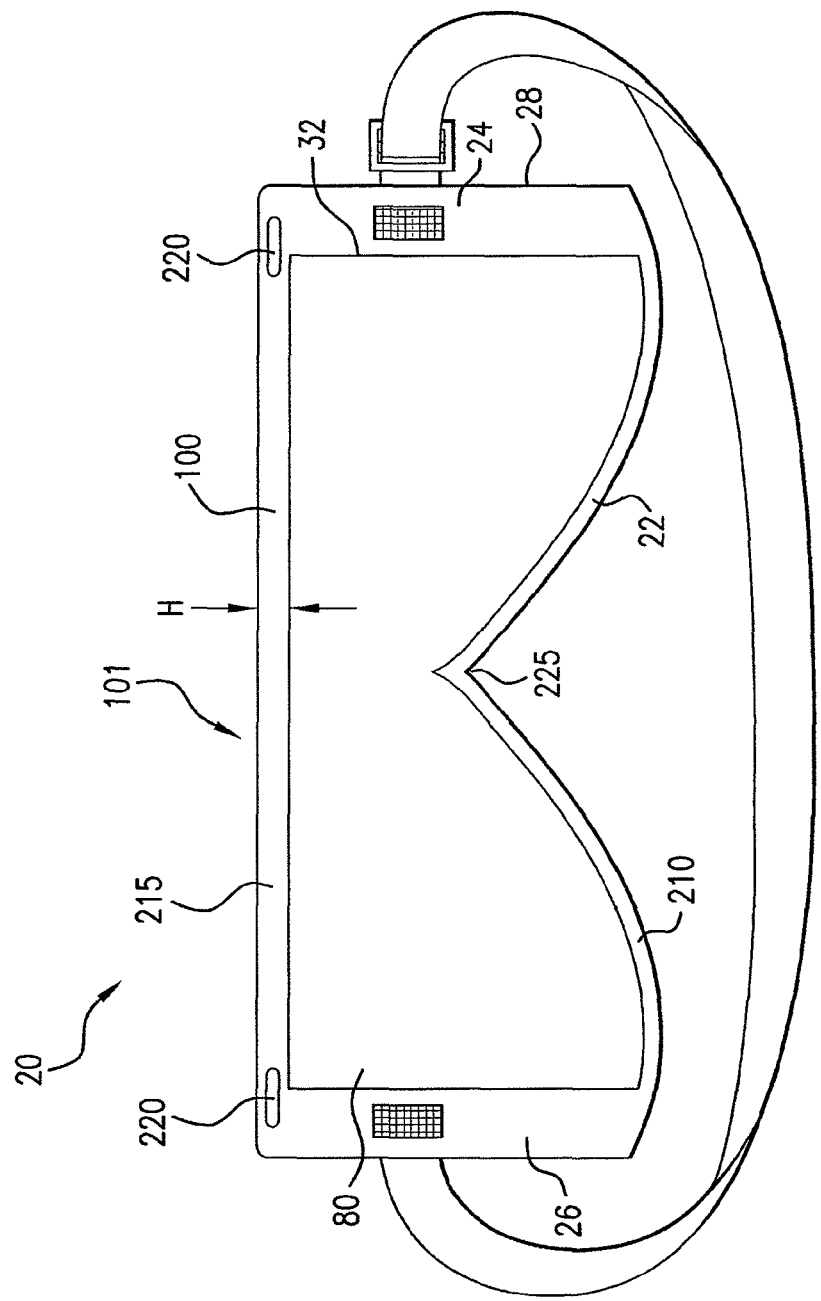
FIG. 2 is a front view of a gel pack according to another embodiment.

In certain embodiments, casing 30 comprises at least two layers of flexible sheets sealed about their edges to form chamber 80. In those embodiments, casing 30 has a periphery defined by the sealed edges of the flexible sheets. The periphery of casing 30 can be co-extensive with the periphery of chamber 80 such that there is no space between chamber 80 and casing 30 as seen in FIG. 1. In other embodiments, as shown in FIG. 2, the periphery is divided into a top lip 101, which can further be divided into a top left lip 100 and a top right lip 215; a bottom lip 103, which can further be divided into a bottom left lip 22 and a bottom right lip 210; a left side lip 24; and a right side lip 26, where the lips are the regions between the outermost edge 28 of casing 30 and the outermost edge 32 of chamber 80 (and therefore such lips contain no gelatinous material).

In certain embodiments, top lip 101 has a height sufficient to accommodate fasteners to attach the gel pack to a support structure (e.g., an external frame), a sheet and/or a strap to hold the gel pack in place. Briefly, the support structure can be used to compress the gel pack against the user's anatomy and optionally to vertically support at least a portion of the gravitational weight of the gel pack when the gel pack is in an applied position. In addition or alternatively, left and right lips 24 and 26 have a length sufficient to accommodate such fasteners. In other embodiments, the bottom lip 103 has a height sufficient to accommodate such fasteners. In other words, the periphery of the casing can be sized to accommodate fasteners in various different locations. With specific reference to the embodiment illustrated in FIG. 2, apertures 220, one defined by top left lip 100 and the other defined by top right lip 215 are shown that can receive fasteners, such as buttons, for example, to fasten the gel pack to a support structure, a sheet, a strap, a heat shield and/or an eye cover. Alternatively, the top lip 101 of the gel pack can have fasteners attached thereto to secure the gel pack to a support structure, a sheet, a strap, a heat shield and/or an eye cover. In certain embodiments, top lip 101 has a height H of between about 2 millimeters (mm) and 20 mm. In other embodiments, top lip 101 has a height H of between about 10 mm and 15 mm. As shown in FIG. 1, gel pack 20 can be configured such that the outermost edge of top portion 40 of casing 30 is coextensive with the outermost edge of the top portion (not shown) of chamber 80 and can still accommodate fasteners. For example, the top portion 40 of gel pack 20 in FIG. 1 can define apertures 280 similar to the apertures of FIG. 2, as long as the edges of the apertures are sealed to prevent leakage of the gelatinous substance.

Figure 3:
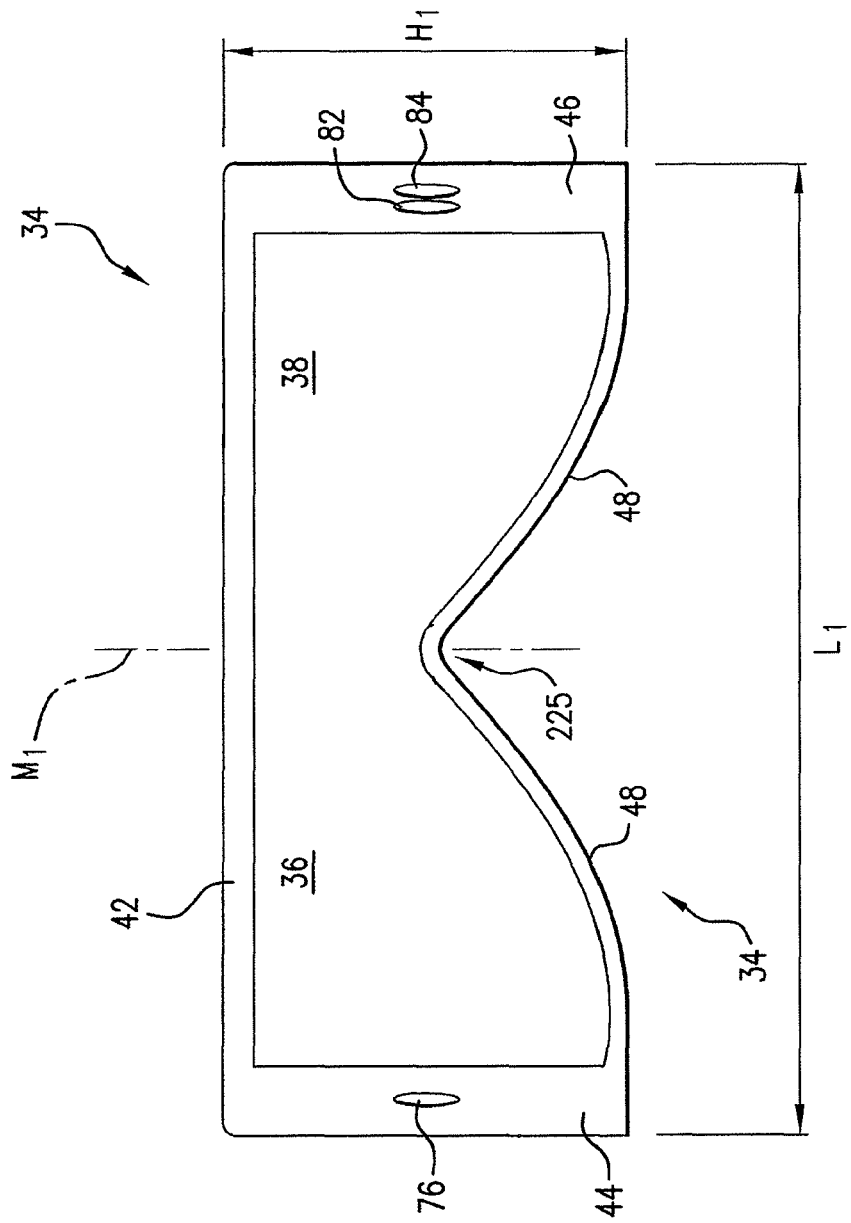
FIG. 3 is a front view of a gel pack according to another embodiment.

The gel pack can have various configurations. Such configurations can depend, for example, on the body region, such as the eye region, of the user that the gel pack is applied against. For example, referring to FIG. 3, a gel pack can be in the form of a mask 34 that is configured to cover the periocular and periorbital regions of the user's face. As shown in FIG. 3, the mask has a generally rectangular configuration with a substantially triangular notch 225 for the nasal area. The mask could have other configurations as well such as a generally oblong configuration with a similar cut out to receive the nasal wings. As shown in FIG. 3, the mask has a centerline $M_1$ dividing the mask 34 into a right section 36 and a left section 38 that spans over both the left and right eyes respectively of the user in an applied position.

Although the left and right sections of a gel pack can be separated from one another such that they are not in fluid communication, in the embodiment shown in FIG. 3, the left and right sections are in fluid communication with each other (i.e. there is no physical separator or divider between the two sections). This feature may be desirable and proved advantageous when the gel pack is activated in a microwave oven and where there is uneven heat distribution applied to the gel pack. Pressure can be applied to the unevenly heated gelatinous substance (i.e. applying back and forth pressure between the two sections of the gel pack) to allow redistribution of the gelatinous substance that resulted in a more homogenous heating effect when in use.

Regarding the specific configuration of a mask that can be used as a gel pack as illustratively shown in FIG. 3, mask 34 has a top portion 42, a right side portion 44, a left side portion 46, and a bottom portion 48. Left and right side portions transition into a bottom portion 48 shaped like a bell curve which defines a notch 225 to accept the nasal wings of the user. Alternatively, the peak of the notch 225 could be angled instead of curved as shown in FIG. 2. As shown in FIG. 3, in some embodiments, mask 34 has a length $L_1$, of between about 4 inches and 11 inches. In other embodiments, mask 34 has a length $L_1$ of between about 5.75 inches and 9.0 inches. In some embodiments, mask 34 has a height H1 of between about 2 inches and 6 inches. In other embodiments, mask 34 has a height H1 of between about 2.5 inches and 4.5 inches.

In some embodiments, the outer edge of the mask 34 (including the top portion 42, the right side portion 44, the left side portion 46 and the bottom portion 48) includes an edge support member. The edge support member is configured to provide vertical support to the mask 34. Said another way, the edge support member supports at least a portion of the weight of the gel pack such that the mask 34 does not buckle when the mask 34 is in a vertical position secured against the eye region of the user. Additionally, in some embodiments, the edge support member helps prevent the outer edge of mask 34 from becoming wrinkled after repeated use. In other embodiments, only a portion of the outer edge of the mask includes an edge support member. For example, in some embodiments, only the top portion of the mask includes an edge support member. In other embodiments, the top portion, the right side portion and the left side portion include an edge support member, but the bottom portion does not.

In some embodiments, an edge support member is made using a piece of 35 gauge polyethylene sized to overlie at least a portion of the top and side sealed edges of an eye mask shaped gel pack. In some embodiments, the width of the edge support member substantially matches the width of the sealed edges of the eye mask shaped gel pack. For example, if the width of the sealed edges of the eye mask is approximately 7 mm, the width of the edge support member would be approximately 7 mm. The gel pack edge and the edge support member can be coupled together. In some embodiments, for example, the gel pack edge is coupled to the edge support member by sandwiching the gel pack edge and the edge support member between two halves of a male-female snap connector. In some embodiments, the combined configuration (of gel pack and edge support member) can be attached to an external frame (described below). For example, in some embodiments, an exposed male-female end of the snap connector used to couple the gel pack edge to the edge support member can be coupled to an exposed male-female end of a snap connector on the external frame. Such an edge support member can improve the ease of handling of the gel pack and the ease of attachment to the external frame.

Figure 4:
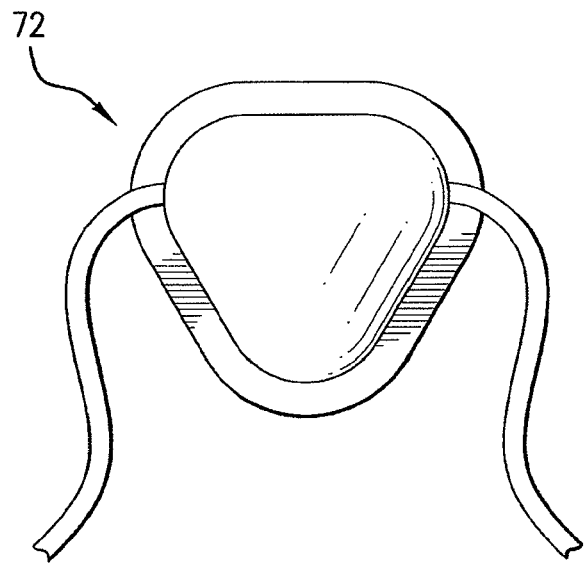
FIG. 4 is a front view of a gel pack according to another embodiment.
Figure 5:
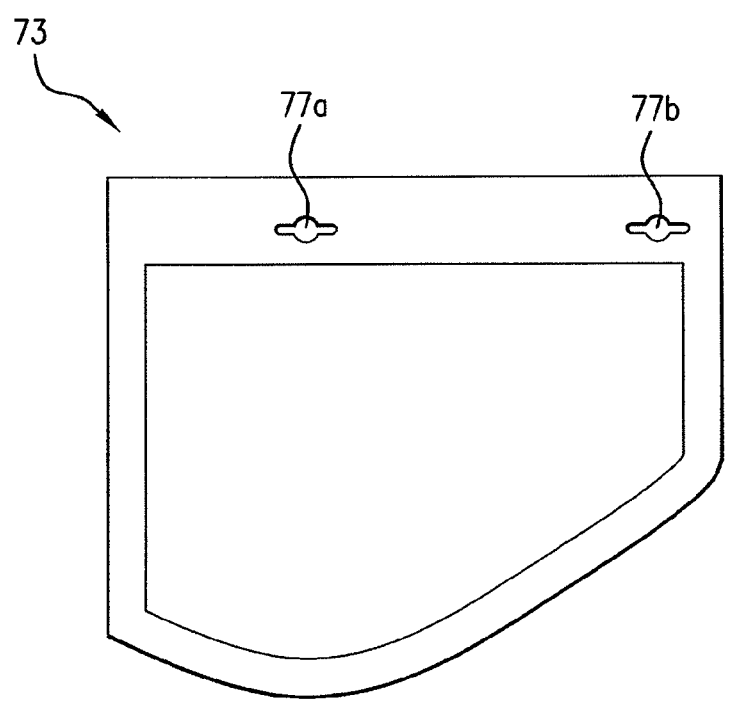
FIG. 5 is a front view of a gel pack according to another embodiment.

Referring to FIG. 4, in other embodiments, a gel pack is in the form of an eye patch 72 which is configured to cover only one eye region of the user (i.e. either the left or the right eye region). Such a configuration may be useful where therapy is desired for only one eye region. In the embodiment shown in FIG. 4, eye patch 72 has an oval shape but other shapes are also possible such as rectangular or circular, for example. As shown in FIG. 5, the exemplary configuration of eye patch 73 can be substantially similar to a single section of mask 34 as shown in FIG. 3, particularly, but not exclusively, if it is desired for the gel pack to cover only one side of the periocular and periorbital regions of the user's face. In the embodiment shown in FIG. 5, the gel pack 73 defines apertures 77a and 77b on the top portion thereon to receive fasteners such as button or snaps, for example, to attach to a support structure, a sheet and/or a strap, as described in more detail below. In other embodiments, the top portion can include other types of fasteners to secure itself to a support structure, a sheet and/or a strap.

Because the gelatinous substance is slippery and difficult to control, a casing is used to contain the gelatinous substance so that the user does not come in contact with the gelatinous substance. The casing can be fabricated from any suitable material to hold the gelatinous substance and to allow thermal diffusion (that is, ready conductivity of heat or cold to the skin, when the gel pack is placed directly or indirectly against the skin). In some embodiments, the casing of the gel pack is fabricated from any suitable material that can withstand repeated exposure to heat and cool with minimal deformation and without significant degradation. In some embodiments, the material is one that is also flexible enough such that it can sufficiently conform to and be in direct contact with the desired eye regions of the user. The material can also be resistant to any negative chemical effects of the gelatinous substance. In some embodiments, the material of the casing is waterproof to protect the casing from exposure to moisture (such as in the case of the gel pack being used in conjunction with moistened sheets as described in more detail below). In some embodiments, the material of the casing can be cleaned with soap and water and/or alcohol pads to reduce the chance of microbial buildup with repeated use.

Non-limiting examples of materials for the casing including thermoplastic polymers films such as polyamides, polyolefins (including polyethylenes and polypropylenes), nylon, biaxially oriented polyamide (BOPA) and/or suitable combinations thereof. Films containing nylon may confer greater temperature conductivity than polyvinylchloride and vinyl materials. Films containing both nylon and polyethylene in a laminate or coextrusion will allow heat-sealing to take place around the periphery of the gel pack, allowing the definition of a heat sealed edge. In some embodiments, a nylon-polyethylene coextrusion approximately 85 microns thick can be used. In such embodiments, the polyethylene component allows the definition of a heat-sealed edge.

Films composed primarily of nylon are more difficult to form into specially-shaped gel packs, such as eye mask shaped gel packs, than are films composed of vinyl or PVC because nylon films are closed with heat sealing, while vinyl and PVC films can be closed with RF (radiofrequency) sealing methods. RF sealing can be easily customized to various shapes over a wide area of material, making production rapid and low-cost, whereas the customization of heat sealing is more difficult, and involves the use of heat seal dies, which can only be adjusted within a set of limited dimensions. Accordingly, most gel packs produced in novelty shapes for cool compress therapy are made from vinyl or PVC.

However, vinyl and PVC materials, when used as casings for gel packs designed for use on the periocular and periorbital regions, have several limitations in comparison to primarily nylon-based films.

Vinyl and PVC can degrade and release potentially toxic plasticizers when heated, for example, in microwave ovens or by other means such as immersion in a hot water bath. Accordingly, the instructions on known gel packs having vinyl or PVC casings include warnings against microwave heating.

Compared to primarily nylon-based gel pack casings, vinyl and PVC-based gel pack casings exhibit poor thermal conductivity to the skin of the user. This limited thermal conductivity can be due to a combination of the thickness of the vinyl or PVC material as well as to its chemical characteristics. Having limited thermal conductivity can be beneficial when the gel packs are frozen (to prevent discomfort to the skin), but it limits the therapeutic effect when the gel packs are cooled, chilled, or applied at room temperature. The limited thermal conductivity of vinyl and PVC-based gel pack casings also limits the therapeutic effect of such gel packs when heated. Because of the limited thermal conductivity, a user would have to warm the gel to a higher-than-needed temperature to produce a given surface temperature of the gel pack. This additional heating can further increase the risk of leaching of plasticizers. Because of the relatively limited amount of the gel in such gel packs, and the relatively narrow therapeutic temperature range for effective thermal treatment to the eye regions, the need for accuracy in gel pack heating, including instantaneous feedback to the touch of the user, is important when heating such gel packs for use.

Vinyl and PVC tend to provide poor barrier functions, allowing water-based gel products to evaporate over time, thereby decreasing the volume of gel in the pack during storage, and especially after use. Nylon-based gel packs, however, substantially maintain their volume and weight even one year or more after manufacture.

Vinyl and PVC can be less comfortable than a nylon-based gel pack casing when used as a heated compress to the eye region. The surface characteristics of vinyl and PVC casings are such that the casings tend to smooth out any small local changes in the height and depth of the gel contents. This is suboptimal when trying to achieve exact conformation to a sensitive body part with significant local contour variations, such as the eye region. In comparison, gel packs with nylon casings are stiffer, having numerous small peaks and valleys in the contour of the casing, which suggests greater conformation to the contour of the eye. Finally, many users find commercially available gel packs with a vinyl or PVC casing to be less subjectively comfortable when placed against the skin, relative to gel packs made with a nylon casing.

As described above, a gel pack includes a chamber that holds a gelatinous substance. The gelatinous thermal substance has characteristics that allow it be malleable enough to conform to the external contour of the user's eye region and to act as an effective thermal reservoir. Specifically, the gelatinous substance can comprise a readily deformable gel that can be repeatedly heated and cooled (including freezing) with no appreciable decrease in performance over time.

Parameters of the gelatinous substance that allow for the maintenance of such intended functions include, for example, the composition of the gelatinous substance, the volume of the gelatinous substance, the surface area of the casing, and/or the viscosity of the gelatinous substance. Regarding the composition of the gelatinous substance, non-limiting examples of gelatinous substances include the gelation of xanthan gum, locust bean gum, gum tragacanth, and guar gum; hydroxypropyl cellulose, absorbent and superabsorbent polymers including CARBOPOL™, carboxymethyl cellulose, sodium polyacrylate; similar materials; and suitable combinations thereof.

In some embodiments, the gel material can include a chemically-activatable solution such as supersaturated sodium acetate trihydrate, which can be used to produce an exothermic reaction and crystallization. In such embodiments, the solution can be actively kneaded by the user to prevent excessive hardening of the material during the crystallization process.

The relationship between the amount of gel and the volume of the chamber within the gel pack can be modified to produce gel packs of different sizes and weights, and with different surface characteristics. Gel packs in which the ratio of gel to chamber volume is relatively low tend to produce packs in which there is relatively little bulging of the surface, and therefore little pressure against the globes of the eyes, but in which the thermal effect of the gel pack is somewhat limited in duration owing to the relatively low volume of gel. Conversely, gel packs in which the ratio of gel to chamber volume is relatively high tend to produce packs in which there is somewhat more of a bulging contour, and hence somewhat more pressure against the globes of the eyes, but in which there is a more lasting thermal effect owing to the larger volume of gel. Thus, one way of increasing the duration of thermal treatment is to increase the volume of gel within the gel pack, either by using more gel in a pack of a given volume, and/or by increasing the volume of the pack.

Referring back to FIG. 1, in some embodiments, a compress assembly can further include a strap 68 attached to casing 30 to secure gel pack 20 against the body region of the user, (which in the embodiment shown in FIG. 1 is the eye region) and to exert a compressive force to the gel pack. The strap can be made of any material sufficient to perform these functions, such as an elastic stretchable material or a non-stretchable material such as a string or ribbon which can be tied to secure the gel pack to the user's face. In some embodiments, the strap is adjustable allowing the user to exert variable degrees of compressive force to the gel pack. For example, an elastic strap can include a buckle 105 to adjust the tension of the strap according to not only the circumference of the user's head but also according to the degree of compression desired to be applied against the user's eye region. In embodiments where the strap is non-elastic (such as, for example, a string or ribbon), the strap can be tightened by pulling on the ends of the strap to control the compressive function of the strap. Other materials and configurations of strap 68 can also be used. In some embodiments, for example, the strap can be made from the same or different material as the gel pack. Referring to FIG. 2, the strap can be attached to the left side lip 24 and the right side lip 26 of casing 30. In other embodiments, strap 68 can be attached to other portions of casing 30 so long as strap 68 performs its intended function. In FIG. 2, strap 68 is threaded through slit 76 (illustrated in FIG. 3) of casing 30 and secured to gel pack 20 via an interference fit with slits 82 and 84 of casing 30 (again illustrated in FIG. 3). However, other means of attaching strap 68 could also be used. For example, the strap could be glued or stitched onto casing 30. In other embodiments, the strap is attached to the casing via a snap. The snap allows the strap to rotationally pivot with respect to the casing, allowing a user to adjust the angle at which that the gel pack applies a force to the user's body. Pivotable points of attachment allow a user to position the strap at any angle without inducing a bend in the strap, which occurs if the strap is attached in a non-pivoting manner.

Alternatively, the strap can be integral with the casing such that the casing and strap are made from the same material and are one-piece in the sense that the strap is not separable from the casing using a normal amount of force without damaging the integrity (i.e. tearing) either the strap and/or the casing. Therefore, strap 68 can be removably or permanently affixed to the casing. Non-limiting examples of material from which strap 68 can be fabricated from include fabrics, plastics, woven elastics, and certain pliable elastic polymers.

Figure 6:
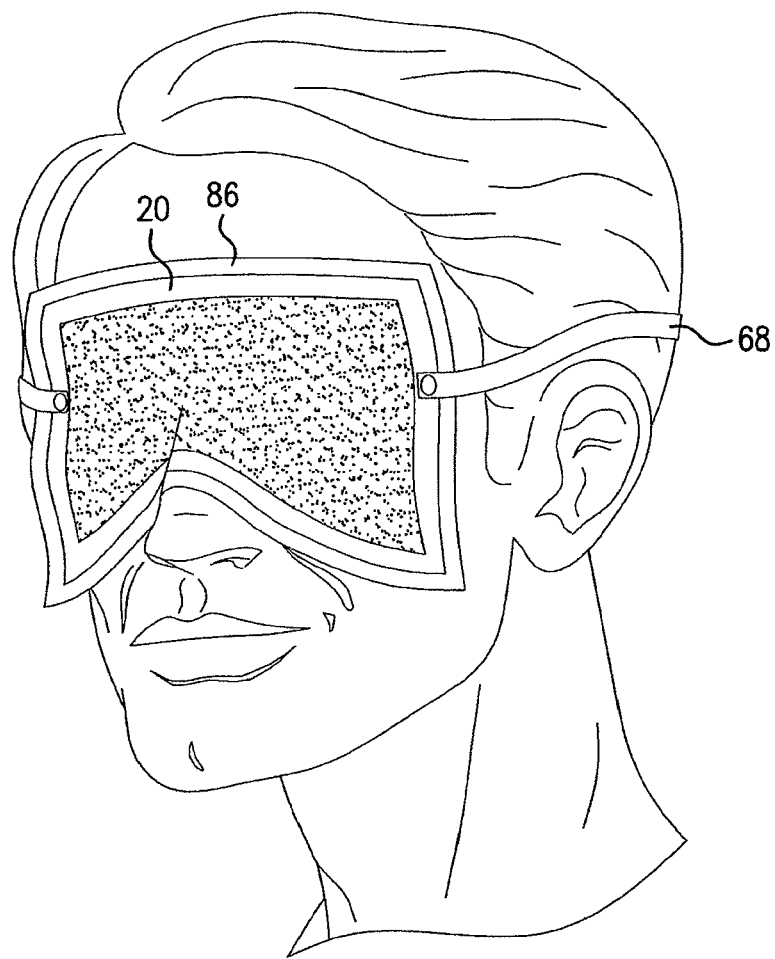
FIG. 6 is a schematic illustration of an assembled eye compress assembly in an applied position according to another embodiment.

In some embodiments, a body compress system and assembly includes a sheet removably disposed on the back side of a gel pack. In the exemplary description described above, the body region is the eye region in which case the sheet may be referred to as a "facial sheet." The sheet serves to provide a wettable cushion between the gel pack container and the user's skin, which cushion can in part serve as a thermal reservoir, but can also serve as a thermal barrier in certain embodiments. In some embodiments, the sheet can be passively disposed on the back side of the gel pack to form an eye compress system, in which the sheet is not removably attached to the gel pack via any mechanical means in a resting position. Instead, as shown in FIG. 6, sheet 86 is held in place during use by being sandwiched between the user's face and gel pack 20, the latter of which is secured to the user's face via strap 68 that is positioned about the user's head. In some embodiments, the facial sheet can be passively disposed on the back side of the gel pack without the use of or the presence of straps, for example, when the user is lying in the supine position.

Figure 7:
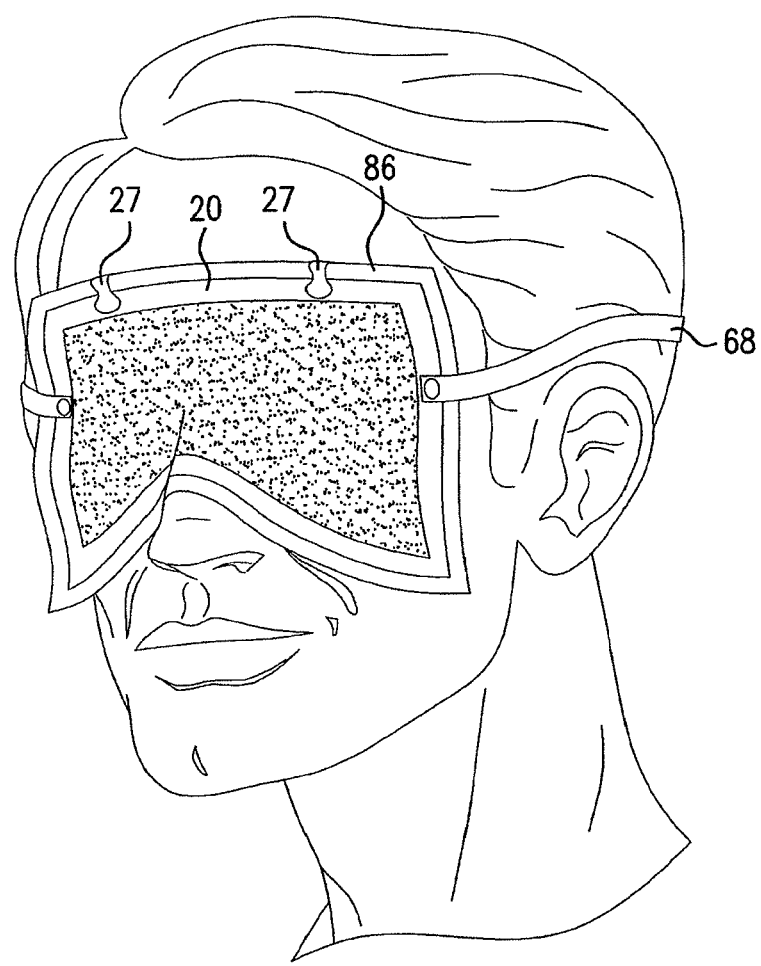
FIG. 7 is a schematic illustration of an assembled eye compress assembly in an applied position according to another embodiment.

Alternatively, as seen in FIG. 7, the sheet can be actively disposed on the back side of the gel pack to form an eye compress assembly in which case the sheet is removably attached to the gel pack via physical means such as at least one fastener 27, which in the illustrated embodiment is a clip, fastens the two components together. In other embodiments, other fasteners can be used including, for example, a male/female fastener, a button, Velcro, a magnetic strip, string, or a snap.

In some embodiments, the sheet used in the compress assembly and system is moistened, disposable, and/or removably positionable between the gel pack and the body region (in this case the eye region) of the user. By "disposable" is meant that a sheet is designed to be used for a small number of cooling and/or heating cycles and then discarded. Specifically, the same sheet is designed to be heated and/or cooled for a maximum of approximately ten times (i.e. ten uses) before being discarded. In other embodiments, a sheet is intended for a single use after which the sheet is discarded. In still other embodiments, a sheet is intended to be used more than ten times before being discarded.

By "removable," "removably positioned" or "removably positionable" is meant that in an applied position, a sheet is not integrally, permanently attached to the gel pack. Thus, a sheet can be removed using a normal amount of force from the back side of the gel pack without disrupting the integrity (i.e. tearing) the gel pack and/or the sheet.

The disposability and removability of the sheet allows for the provision of a fresh and hygienic surface when the user decides to change the sheet (either at every use, or after a few uses). Frequent exchanges of used sheets with fresh sheets can minimize the risk of infection when re-using the compress assembly or system. The use of new sheets can be especially important when sharing the compress assembly or system with another person. Antimicrobial agents and/or preservatives can be added to the sheet and can aid with prevention of bacterial buildup. The removability and disposability of sheets also provides a more economical method of use, with the relatively inexpensive sheets being replaced after a small number of uses, while the relatively more expensive gel pack can be reused multiple times. The use of removable sheets may also allow the user to choose from a variety of types of pre-medicated sheets, according to his or her needs, during each therapeutic treatment session.

In some embodiments, the sheet is impregnated with various chemical agents designed to improve the health of the skin or the health of other tissues or organs that may be present in the body part intended for thermal compress therapy, or even to reduce injury to those tissues or organs that may result from repeated thermal compress therapy. Such chemicals and their targeted therapies, including those described below under the description of moist sheets, can be impregnated into the sheet, which can either be used dry or can be moistened prior to use.

Although the sheets can be dry, in some embodiments, the sheet is moistened. In some embodiments, the sheet is pre-moistened such that the user need not moisten the sheet before use. In embodiments where the sheet is moistened, the sheet material can be water-absorbent and resilient enough to withstand long periods in a moistened state between the time of manufacture and the time of use without disintegrating. Such a material would also be expected, in its moistened state, to be subjected to manipulation and pulling without significantly tearing or deforming. For instance, a sheet can be subjected to the normal amount of manipulation and pulling necessary to adjust the sheet in relation to the gel pack and optionally with respect to an external support structure (as described in more detail below) during a single use period, which can last between about 2 minutes and 30 minutes. Such manipulation might include repeatedly attaching and detaching a sheet from the external support structure. The sheet material can retain moisture reasonably well, rather than display rapid evaporation, so that users may benefit from a prolonged application of the moist thermal effect. For example, once removed from a dispenser and applied against the user's body region, the sheet material can retain at least 60% and, in some embodiments, at least 70% and, in other embodiments, at least 80% of its moisture content for at least a 5 minute period of time.

In embodiments where the sheet is moistened, the sheet can be impregnated with various chemicals that may serve a purpose in thermal compress therapy for a particular body part. In some embodiments, for example, the chemicals can improve the baseline condition of the body part and/or reduce any injury that can be caused by repeated use of moist or dry thermal therapy. The presence of chemicals can, for example, mitigate chapping and/or drying out of skin that can occur if water is used as the moistening agent. In treatment of the eye region, for example, chemical treatments can target such tissues as the periorbital skin, external skin of the eyelids, meibomian glands, punctae, conjunctiva, and cornea. In some embodiments, for example, an eye compress can contain chemicals such as, but not limited to, water, moisturizers, humectants, emollients, nutrifying agents, surfactants, detergents, cleansers, neutraceutical formulations, fragrances and aromatherapeutic compounds, antimicrobial and anti-parasitic compounds, preservatives and buffers, and/or other agents. Specifically, for ocular use, certain chemicals can be selected that may be generally therapeutic for ocular conditions, such as surfactants and humectants that are complementary to molecules normally produced on or near the eyes, as well as chemicals that are therapeutic in specific ocular uses, such as antihistamines, mast cell stabilizers, antibiotics, antiparasitics, corticosteroids, immunomodulatory agents, antiviral agents, and other medications.

Figure 8:
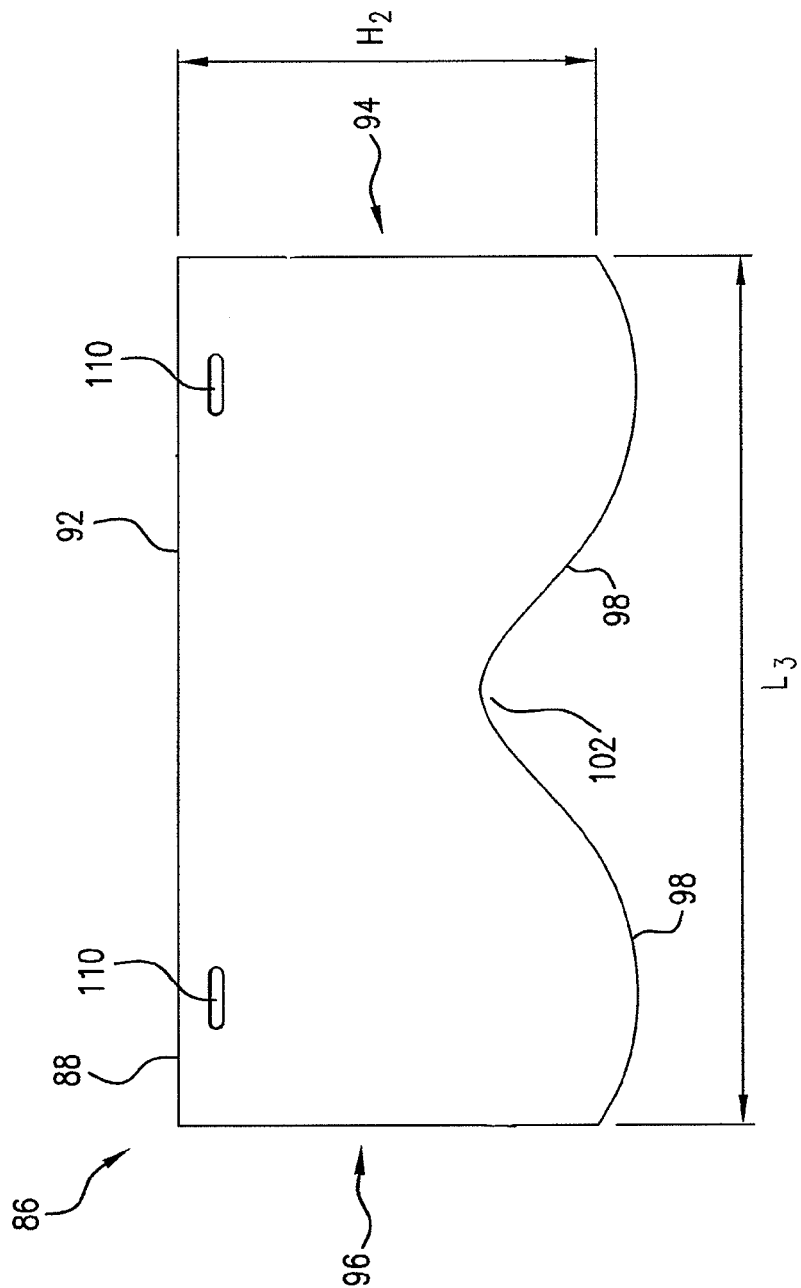
FIG. 8 is a front view of an exemplary sheet according to another embodiment.

Referring to FIG. 8, an exemplary facial sheet 86 according to an embodiment of an eye compress assembly and system comprises a sheet body 88 that has a top portion 92, a left side portion 94, a right side portion 96 and a bottom portion 98. In the embodiment shown in FIG. 8, the right and left side portions transition into a bottom portion shaped like a bell curve which defines a curved cut out 102 to accept the nasal wings of the user. Alternatively, the peak of the cut out can be angled instead of curved (similar to the notch 225 of gel pack 20 shown in FIG. 2). In some embodiments, sheet 86 mimics the outline of the gel pack that is used with the sheet as part of the eye compress kit. In some embodiments, a sheet is sized and shaped to extend beyond the edges of the gel pack on all sides so that the user's face is contacted in all applied areas by the facial sheet rather than directly by the gel pack. In some embodiments, for example, sheet 86 can have a length $L_3$, of between approximately 5 inches and 11 inches. In some embodiments, for example, sheet 86 can have a height $H_2$ of between approximately 2 inches and 6.5 inches.

As shown in FIG. 8, in certain embodiments, top portion 92 of sheet body 88 defines openings 110 to accommodate fasteners to attach a sheet to a gel pack and/or a support structure (described in more detail below). The support structure can be used to vertically support at least a portion of the gravitational weight of a sheet when the sheet is in use (in an applied position). The openings can be defined in different locations of sheet body 88 as described above with respect to gel pack 20. Similarly, as described above with respect to a gel pack, the sheet body can have fasteners attached thereto to secure a gel pack or a gel pack and an external support structure, such as, for example, tabs, snaps, Velcro and/or the like.

A sheet can be fabricated from a suitable biocompatible material. In some embodiments, a sheet material can be soft in texture, thereby exposing the user's skin to a surface that is more comfortable than the slick, non-moist casing of the gel pack. In some embodiments, a sheet material will also have a slight cushioning effect to reduce the impact of the gel pack against the user. In some embodiments, a sheet will sustain its integrity after being stored in a moistened state for up to several months, and will be resilient enough to resist tearing or ripping when attached to fasteners that removably affix it to the surface of the gel pack.

The use of dry paper towels, cloth towels, and gauze pads under such gel packs as part of eye compress therapy is known. It is typically recommended that the materials are placed directly under the gel pack without being moistened. This tends to provide a thermal barrier to heat therapy. Because these substances are provided in a dry form, this also provides a form of dry heat.

Hypothetically, such materials might be provided in a moist or wet form for use under a hot gel pack. In particular, the user might be instructed to moisten the materials prior to insertion under the gel pack. However, this would inconvenience the user. First, both the degree of moisture and the temperature of the water varies from one application to the next. This variation in moisture causes variations in the response of the material to being microwave-heated, thus making it more difficult for the user to arrive at a standard microwaving time for all treatments. Second, moistening the skin of certain users with water alone, during sustained and repeated use of hot compresses, can damage the skin (such as through chapping) and/or be of limited utility in treating various specific conditions of the eyelids and periorbital skin. Providing chemicals such as emollients, skin nutrifying agents, cleansers, and the like can reduce skin damage and provide treatment to various conditions. Third, the mechanics of packaging such materials (that is, dry paper towels, cloth towels, and gauze pads) in a pre-moistened form to the user can be difficult and expensive, because these materials are not typically intended for long-term storage under moistened conditions.

In some embodiments, the sheet is fabricated from a non-woven fabric. In other embodiments, the sheet can be fabricated from any material configured to perform the intended functions. For example, the sheet can be fabricated from woven or knitted fabrics, fibrous fabrics, films and foams.

As used herein, the term "non-woven fabric" means an assembly of fibers held together by means and/or processes other than those used in traditional weaving processes. Processes used in the creation of non-woven fabrics include, but are not limited to, mechanical interlocking in a random web or mat, thermal fusing of fibers, or bonding with a cementing medium such as starch, glue, casein, rubber, latex, or one of the cellulose derivatives or synthetic resins.

The non-woven fabric can be prepared from fibers of any fibrous or fiber forming polymer. Synthetic fiber forming materials can be made from the polymers of classes which include, but are not limited to, polyolefin, polycarbonate, polyacrylate, polymethacrylate, polyester, polyamide, polyaramide, polypropylene, polyurethane and the like, as well as copolymers of the above materials. Modified natural polymers such as but not limited to regenerated cellulose and chitin can also be used. Additionally, natural polymeric fibers can be used which include, but are not limited to, cotton, jute, ramie, hemp, other forms of cellulose and forms of chitin. However, a non-woven fabric does not include a paper towel. The non-woven fabric can be prepared by techniques including, but not limited to spun bonding, melt blowing, hydro-entangling, hydro-lacing, electrostatic spinning, needling, felting, wet laying and the like.

In some embodiments, the non-woven sheet is composed of spunlace. In some embodiments, the spunlace has a weight of approximately 20 gsm to 150 gsm. In other embodiments, the spunlace has a weight of approximately 40 gsm to 120 gsm. In still other embodiments, the spunlace has a weight of approximately 50 gsm to 80 gsm. The sheets with the referenced weights hold moisture well and are comfortable against the skin.

In some embodiments, the sheet is a pre-moistened, non-woven fabric sheet. A pre-moistened non-woven fabric sheet may be desirable as the amount of user-supplied moisture may tend to be non-uniform between uses, thereby producing unpredictable heating from one use to the next. In contrast to user-moistened fabrics (such as cloth towels including terry cloth towels), removable non-woven fabric sheets can be easily packaged together and pre-moistened in such a way that each sheet taken from the package will contain a relatively predictable amount of moisture. This established amount of moisture may produce a more predictable and therefore safer result when a sheet is treated with a given amount of heat. In particular, this established amount of moisture may produce a more predictable and therefore safer result when the sheet is treated with a given amount of microwave irradiation as a means of heating the sheet (with or without a gel pack).

Experimental use of moistened non-woven sheets adapted for use on an exemplary eye compress assembly has been performed. As shown in Example 1, wet non-woven sheets achieve better thermal conductivity than dry non-woven sheets. Such a result was unexpected because prior teaching has suggested that it is best to keep the sheet dry, suggesting that moisture on the sheet serves as a thermal barrier, reducing the thermal effectiveness of the gel pack.

In the particular application of microwave activation for heat therapy, the moisture-containing sheets may be desirable as it was found that moistened sheets improve the even distribution of heat throughout the microwaved gel pack. The moist sheets can act more homogeneously in relation to microwave irradiation and, as the sheet heats up, it can pass this homogenous heating to the gel pack. Such a characteristic is unexpected since the sheet has a lower water content than the gel pack and would not be expected to influence the gel pack heating. The basis for this discovery is presented in Example 4.

Paper towels have been recommended for use with gel pack systems for ocular compress therapy. Dry paper towels, however, typically have rough or "pebbled" surfaces, which can be uncomfortable when held against the user's skin. On the other hand, a non-woven fabric sheet has been found to have an unexpected "springiness," despite its relatively thin profile, that paper towels do not have. This produces a cushioning effect when the sheet was interposed between the user's face and a gel pack.

As shown in Example 2, non-woven sheets outperformed paper towel sheets in testing on an exemplary eye compress gel pack system, achieving greater water absorbency, longer moisture retention, and greater resiliency when wet. The water absorbency and moisture retention were unexpected, because paper towels are specifically marketed as being superior at cleaning up spills, whereas non-woven sheets are typically marketed as having superior dirt-cleaning properties. Because it is anticipated that users may prefer to re-use sheets during a particular eye compress treatment session (which may last 20 minutes or more), and because it is also anticipated that users will subject moist sheets to microwave heating, which increases evaporation rates, a sheet with longer drying-time is desirable.

A non-woven material also has advantages over a woven cloth material, such as a terrycloth material. For example, Example 3 illustrates the greater thermal barrier posed by a woven sheet (terrycloth towel). In daily use, knitted and woven materials tend to present an increased risk of infection relative to non-woven fabric sheets due to reuse of the material and the tendency for users to share such materials.

In experiments, an exemplary device designed for heated eye compress therapy and fitted with moistened non-woven fabric sheets sustained a given temperature much longer than did a washcloth heated under hot water. Because there was no need to interrupt treatment for re-heating of the gel pack, the desired therapeutic goal was achieved in a much shorter time, thus proving of greater convenience to the user.

In some embodiments, a dry sheet or layer is disposed between the wet sheet and the body of the user, or between the gel pack and the wet sheet, and is prepared such that it covers a specific area. For example, the dry sheet or dry layer can have slits configured to be positioned over the eyelid margins. This allows for selective transmission of moist heat to the eyelid margins only. Similarly, in some embodiments, sections of a dry sheet or layer that covers the periorbital regions contains internal openings that are sized and shaped for the periocular regions. By covering the periorbital regions while having openings over the periocular regions, the sheet or layer allows selective transmission of a thermal effect to the periocular regions alone. Conversely, a system could be devised to conduct heat only to the periorbital regions. In other embodiments, a single sheet can be pre-treated so that it has both wettable and non-wettable areas that achieves the same effects as the two-sheet method described above. In other words, the wettable area of such a sheet selectively transmits thermal therapy to the target tissues underlying the wetted areas, and has a thermal barrier effect over the tissues underlying the non-wettable areas. The selective application of heat can also be applied such that the portion of the facial sheet that covers the nasal region is kept dry, to reduce the amount of heat transmitted to this particular area, for the comfort of the patient. In some embodiments, the above embodiments of removable layers or sheets can be modified so that they are permanently applied to a gel pack or to an external support structure (such as an external frame as described in detail below). The experimental basis of these approaches can be found in Example 1. As discussed below, a heat shield can be used to achieve selected thermal transmission to targeted areas.

In some embodiments, the compress assembly and system further include an external frame actively or passively positioned against the front side of a gel pack. Specifically, the external frame is attachable to or otherwise positionable against the outwardly facing side of the gel pack (i.e. the side of the gel pack that will not be in contact with the patient's body region in an applied position of the gel pack). Specifically, the external frame is passively positionable on the outwardly facing surface of the gel pack to form a body compress system or actively positionable on the outwardly facing surface of the gel pack to form a body compress assembly. By being passively positionable against the gel pack, the external frame is positioned against the gel pack without the use of any mechanical means to attach the external frame to the gel pack in an applied position of the system. However, the external frame can be in communication with the gel pack via frictional engagement. By being actively positionable against the gel pack, the external frame is positioned against the gel pack via the use of mechanical means to attach the external frame to the gel pack in an applied position of the assembly.

In some embodiments, the external frame includes a strap to compress the gel pack against the user's anatomy and provides a relatively firm base surface (as compared to a flexible surface such as is supplied by an elastic and/or a soft woven fabric) that is designed to provide a source of external pressure against the gel pack directly over specific regions of the anatomy of the user. The user can then adjust the pressure of the external frame in order to optimize pressure against the body part. Thus, for example, in a body compress system designed for use on the eye region in which a gel pack is positioned against the eye region with the user in an upright position and in which the gel pack does not have a source of vertical support for its weight, an external frame that is passively positionable against a gel pack can be shaped to correlate with the general outline of the ocular anatomy (or to some portion thereof) in such a way that any increased pressure on the external frame transmits pressure to the ocular anatomy (or to some portion thereof). During use, the stiffness of the external frame provides some support to keep the gel pack in position against the body part. The stiffness of the external frame also allows the user to position the frame in such a way that the lower edge of the frame rested on a body part inferior to the body part being treated, such that the bottom of the gel pack was supported on the junction between the bottom edge of the external frame and the user's body. This allows the user to select from a variety of compression tensions in a strap that tightened the external frame against the gel pack. The stiffness of the external frame can also make it easier for the user to determine and adjust the exact location in which pressure is to be exerted, simply by pressing the relatively stiff frame element with his or her hands.

In some embodiments, the external frame defines relief apertures corresponding to the region of the eyes themselves. The presence of such relief apertures selectively decreases the direct pressure of the external frame against the eyes, and allows the user to directly manipulate the gel pack by providing direct access through the relief apertures.

In embodiments where the external frame is actively positionable against the gel pack, the gel pack or the external frame includes a strap and the external frame is fastened to the gel pack to support at least a portion of the gravitational weight of the gel pack so that in an applied position, the gel pack does not sag to such a degree that the gel pack in no longer able to provide therapeutic benefit to the user. Such sagging can take place both in terms of the position of the entire gel pack as well as in terms of the gelatinous material within the gel pack.

Figure 9:
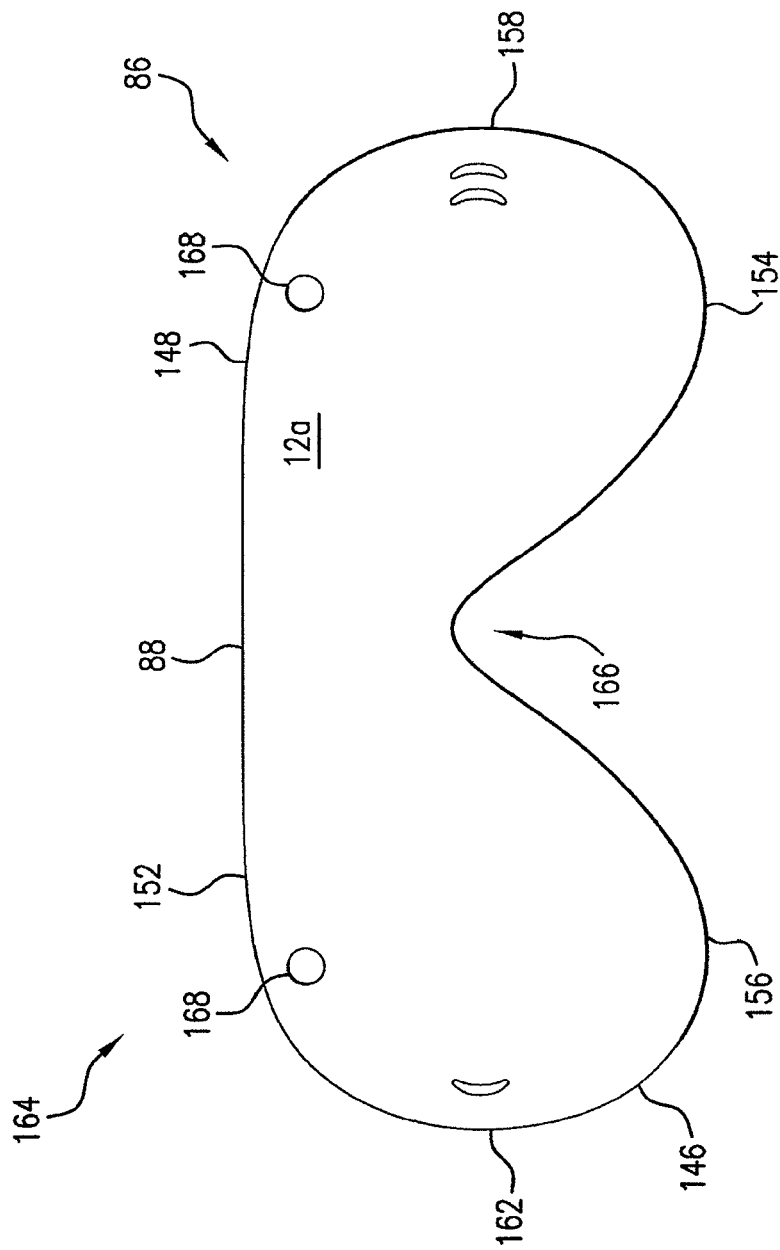
FIG. 9 is a front view of an external frame according to another embodiment.

As seen in FIG. 9, in an embodiment, external frame 164 comprises a frame body 146 having a top left portion 148, a top right portion 152, a bottom left portion 154, a bottom right portion 156, a left side portion 158 and a right side portion 162. In some embodiments, the external frame can mimic the outline of the gel pack that is used with the external frame as part of the eye compress assembly or system. For example, the right and left side portions can transition into a bottom portion shaped like a bell curve which defines a curved or angled cut out 166 to accept the nasal wings of the user. In some embodiments, the external frame is sized and shaped such that the gel pack extends beyond the edges of the external frame on all sides so that the user's face is contacted in all applied areas by the gel pack rather than directly by the external frame. Similarly, referring to FIG. 11, in embodiments where a facial sheet is used, the external frame 164, gel pack 20 and facial sheet 86 have similar outlines with facial sheet 86 having a greater surface area than gel pack 20 and gel pack 20 having a greater surface than the external frame 164.

Figure 10:
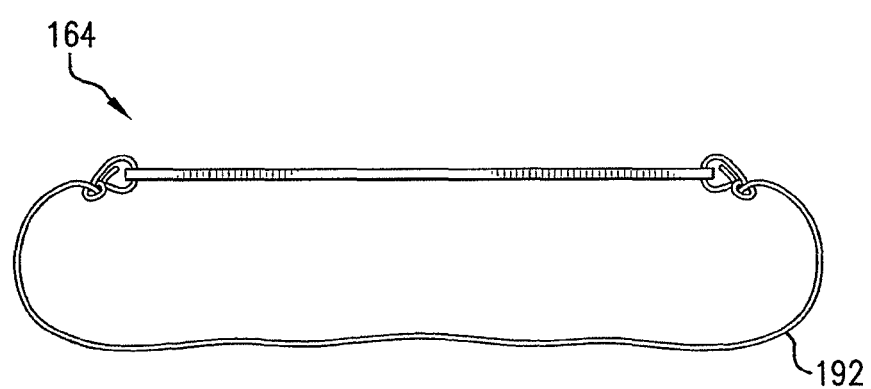
FIG. 10 is a plan view of an external frame having a generally planar configuration in a resting position.

In certain embodiments, the external frame assumes a generally flat or planar conformation when in a resting position. As used herein, a "resting position" refers to the position of the external frame when it is not applied against the body region of the user (i.e. an applied position) and is resting on a flat surface. This resting position of an external frame can be seen best in FIG. 10, which is a plan view of the external frame 164 of FIG. 9 (but also including a strap 192). In embodiments where the external frame has a generally planar configuration, when the eye compress assembly is applied against the eye region, the external frame has the ability to press the gel pack directly against the desired eye regions (i.e. the periocular and/or periorbital region of the face). In other embodiments, the left side portion of the frame and the right side portion of the frame are arc-shaped, as described in further detail herein.

As described above, in some embodiments, the external frame can be attached to the gel pack to support at least a portion of gravitational weight of the gel pack such that the gel pack does not sag on the user's face to such a degree that the gel pack no longer is able to provide therapeutic benefit. In such an embodiment, the external frame is fabricated from a material stiff enough to support at least a portion of the weight of the gel pack such that the external frame does not buckle when the gel pack is attached to the external frame and the external frame is in a vertical position secured against the eye region of the user. An external frame can be attached to the gel pack in any suitable way. For example, the external frame can be permanently or removably attached to the gel pack in use. Regarding the former, an external frame can be glued or heat molded onto the gel pack during manufacture. Other means of permanently attaching an external frame to the gel pack are also possible. If an external frame is permanently attached to the gel pack, the external frame can be fabricated from a material that is heat and cold resistant such that the external frame can be exposed to a heat or cold source without degrading to the point of losing its intended functions.

Regarding an external frame being removably attached to the gel pack in use, the frame can accommodate at least one fastener to secure the gel pack to the external frame. For example, as illustrated in FIG. 9, the external frame can define apertures 168 in top portion 148 and 152, respectively, of frame body 146 that are configured to receive buttons, string, snaps or other fasteners to attach to the top portion of the gel pack, in which case the external frame supports substantially all of the gravitational weight of the gel pack. Although FIG. 9 illustrates two apertures, an external frame can include more than two apertures in the top portion of the frame body. An external frame can also define any suitable number of apertures in bottom right and left portions 156 and 154 respectively and/or right and left side portions 162 and 158, respectively. Alternatively, external frame 164 can define a single aperture centrally located between top right portion 152 and top left portion 148. Still alternatively, the external frame can define at least one aperture on left side portion 162 and at least one aperture on right side portion 158 of frame body 146. In such an embodiment, the frame body supports at least a portion of the gravitational weight of the gel pack (but not as much as would be supported if the gel pack were attached to the top portion of the frame body). However, the gravitational weight that is supported in such an embodiment is enough to prevent the gel pack from sagging during use. The exact number and location of the apertures can vary so long as an external frame supports enough of the gravitational weight of the gel pack such that the gel pack does not sag in an applied position. Notwithstanding the exact number and location of apertures in external frame 164, the gel pack and/or sheet can have similar apertures, for example, as described above such as with respect to FIGS. 2 and 8.

Figure 12:
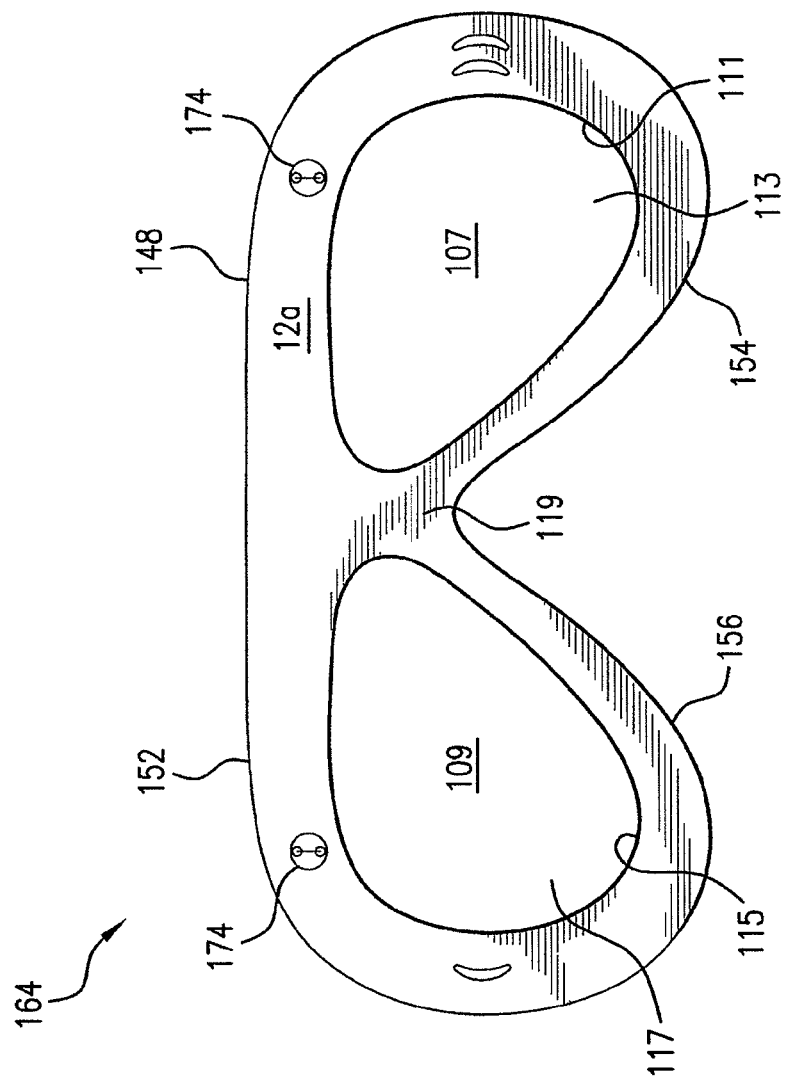
FIG. 12 is a front view of an external frame according to another embodiment.

In addition to being designed to receive separate fasteners that are applied to the frame body, the frame body can contain fasteners that are already attached or attachable to the frame body. For example, the frame body can accommodate a magnetic strip to attach to a magnetic strip or metal strip disposed on a gel pack. In turn, a sheet can have a magnetic strip or metal strip to attach to the gel pack. In certain embodiments, as shown in FIG. 12, external frame 164 can have buttons, snaps and/or other fasteners already attached to the frame body. Such fasteners can be die-cut or molded, for example, into the frame body of the external frame. For example, FIG.

12 shows buttons 174 attached to the frame body of external frame 164. The aforementioned fasteners are only exemplary and other fasteners can also be used so long as they achieve the function of attaching a gel pack and/or a sheet to an external frame. Further any number of fasteners can be used to secure the components of the eye compress assembly. Non-limiting examples of other types of fasteners include velcro, clips, snaps and male/female fasteners.

In some embodiments, an eye compress kit can include separate fasteners that are not integral with the external frame but rather separable in the sense that the fasteners can be separated from the external frame without disrupting the integrity of the external frame or fastener (i.e. tearing or breaking the external frame or fastener). An example of such separable fasteners include clips as shown in FIG. 7. In some embodiments, the fasteners are attached or attachable to the top portion of the frame body although the fasteners can be positioned at different locations on the frame body as described above with respect to apertures defined by the frame body to receive fasteners.

As described briefly above, in embodiments where a facial sheet is desired to be actively placed between the user's eye region and the gel mask, the facial sheet can also be configured to receive fasteners. For instance, as shown in FIG. 8, the top portion of the facial sheet can define apertures 110 to accommodate the same fasteners used to secure the gel pack to the external frame. In other embodiments, the facial sheet is not configured to be attached to the gel pack or the external frame.

Figure 11:
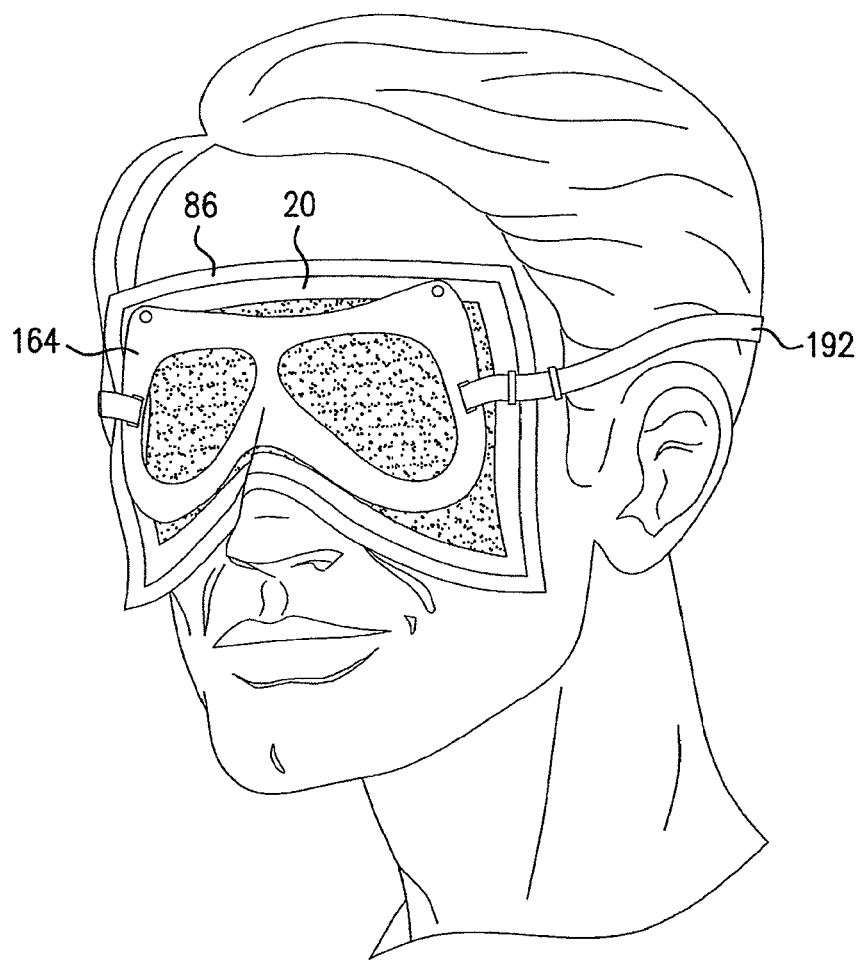
FIG. 11 is a schematic illustration of an assembled eye compress assembly in an applied position according to another embodiment.

An eye compress assembly that includes an external frame can also include a strap 192 as shown in FIG. 11. The strap can be attached to the gel pack or the external frame but in the embodiment shown in FIG. 11, strap 192 is attached to the left and right portions of the external frame 164. In this embodiment, the strap is adjustable (although it is not required to be in other embodiments) such that tightening or loosening of the strap exerts a controllable horizontal pressure on the external frame. In certain embodiments, where the external frame is not attached to the gel pack via fasteners but is rather passively positioned against the user, the external frame serves the function of applying compressive force against the user's anatomy. However, in certain embodiments, where an external frame and a gel pack are attached together via at least-their top portions, the horizontal pressure exerted by the external frame strap is largely independent from the vertical support provided by the external frame to the gel pack via the one or more fasteners at the top portion of the eye compress assembly. To achieve this effect, in certain embodiments, an external frame can include slits in the right and left side of the external frame to accommodate a strap (such accommodation being similar to that described above with respect to a gel pack). In fact, in certain embodiments, both the gel pack and the external frame have slits in alignment with each other such that a strap can be threaded through both the gel pack and external frame for added securement of the gel pack to the external frame.

Alternatively, a strap can be attached to an external frame via other exemplary means such as by being stitched or glued onto the external frame (again, such exemplary means being similar to that described above with respect to a gel pack). Therefore, the strap can be permanently or removably attached to the external frame. The strap can be made of a variety of stretchable or non-stretchable materials that will not be either adversely affected by low levels of heat or heated by low levels of microwave irradiation such as the amount required to heat the gel pack, including fabrics, plastics, woven elastics, and some pliable elastic polymers. In some embodiments, the strap is able to be loosened sufficiently so that the external frame can serve simply to support the gel pack and soft sheets in relation to the body part, without compressing them against the body part. In general, the description of a strap as described above with respect to a gel pack applies to a strap attached to an external frame instead.

Figure 14:
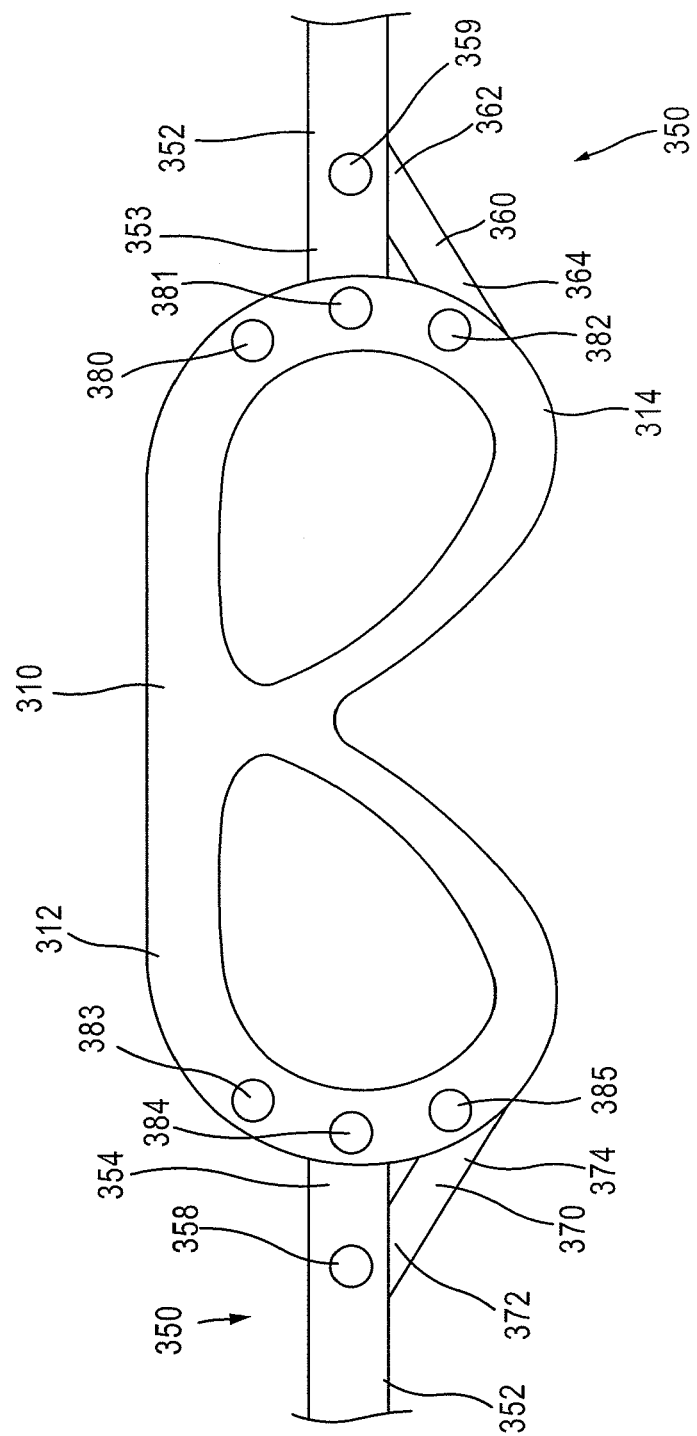
FIG. 14 is a front view of an external frame in a first configuration, according to another embodiment.
Figure 15:
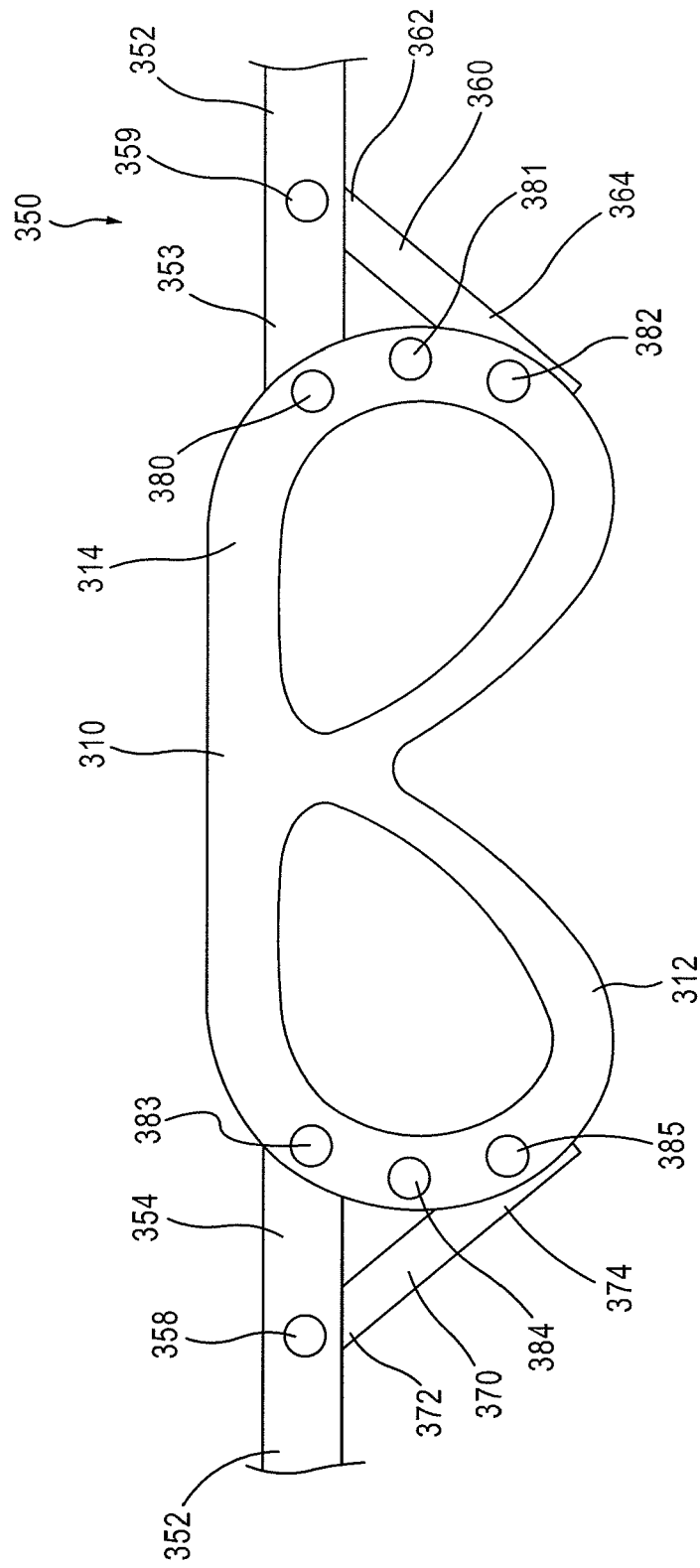
FIG. 15 is a front view of the external frame of FIG. 14 in a second configuration.
Figure 16:
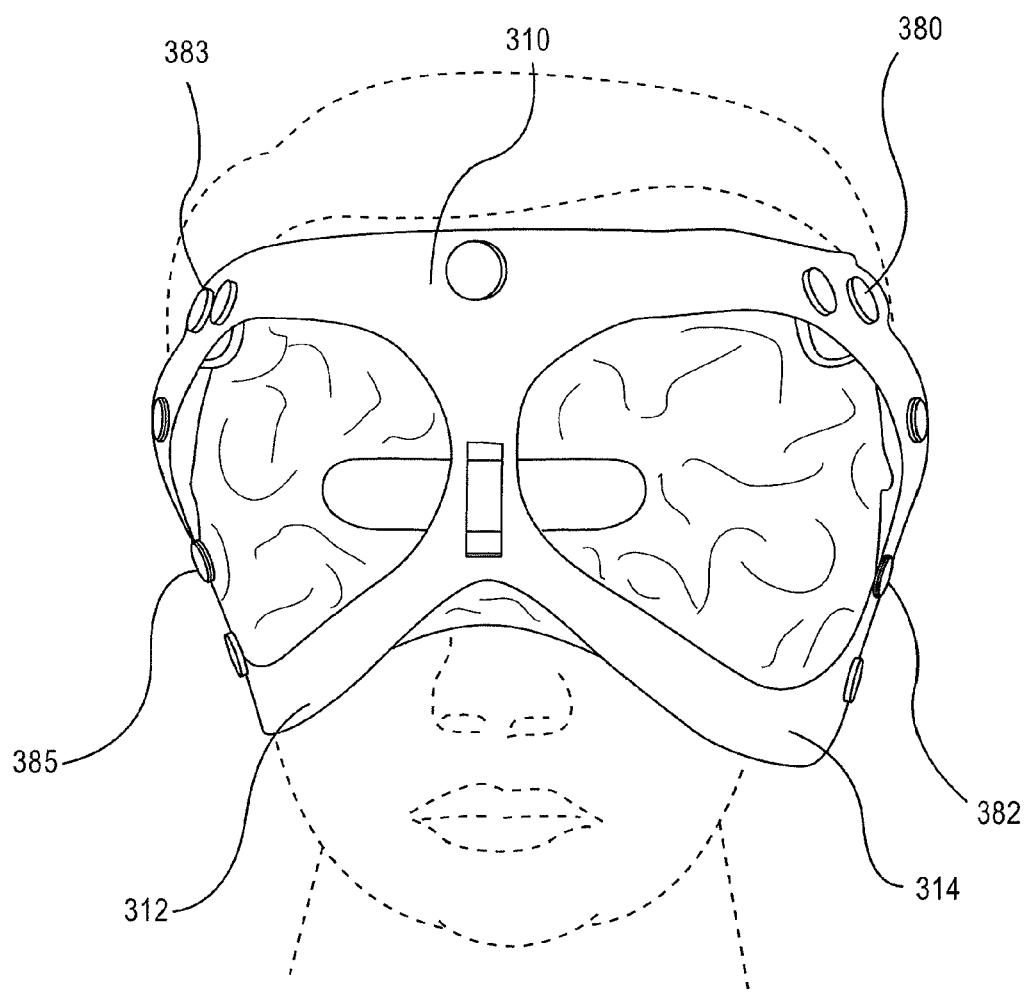
FIG. 16 is a schematic illustration of the external frame of FIG. 14 in the second configuration in an applied position.

FIGS. 14-16 show an external frame 310 coupled to a strap system 350 in a first configuration (FIG. 14) and a second configuration (FIG. 15). The external frame 310 includes a left side portion 314 and a right side portion 312, and is similar to the external frame 164 shown and described with respect to FIG. 12. The left side portion 314 includes a first fastener 380, a second fastener 381, and a third fastener 382. Similarly, the right side portion 312 includes a first fastener 383, a second fastener 384, and a third fastener 385. The fasteners, 380-385, are configured to attach the external frame 310 to a portion of the strap system 350, as described in further detail herein.

The fasteners, 380-385, can be constructed of any suitable coupling mechanism. In some embodiments, the fasteners 380-385, are male/female snap connectors configured to releasably couple the strap 352 to the external frame 310. In other embodiments, the fasteners, can be other types of releasable coupling mechanisms such as male/female fasteners, buttons, Velcro, magnetic strips and/or strings. In other embodiments, the fasteners can include toothed rungs that allow a user to slidably adjust the position of the strap. In still other embodiments, the fasteners can be configured to permanently attach the strap to the external frame.

The strap system 350 includes a first strap 352, a second strap 360, and a third strap 370. The first strap 352 includes a first end portion 353 and a second end portion 354. The first end portion 353 includes a fastener 359 configured to couple the first end portion 353 of the first strap 352 to a first end portion 362 of the second strap 360. Further, the first end portion 353 of the first strap 352 is configured to be coupled to the left side portion 314 of the external frame 310 via the first fastener 380 (when in the second configuration as shown in FIG. 15) or the second fastener 381 (when in the first configuration as shown in FIG. 14).

Similarly, the second end portion 354 includes a fastener 358 configured to couple the second end portion 354 of the first strap 352 to a first end portion 372 of the third strap 370. Further, the second end portion 354 of the first strap 352 is configured to be coupled to the right side portion 312 of the external frame 310 via the first fastener 383 (when in the second configuration as shown in FIG. 15) or the second fastener 384 (when in the first configuration as shown in FIG. 14).

The second strap 360 includes a first end portion 362 and a second end portion 364. As described above, the first end portion 362 is configured to be coupled to the first end portion 353 of the first strap 352 via fastener 359. In some embodiments, the fastener 359 is a snap connector that allows the second strap 360 to rotationally pivot with respect to the first strap 352. In other embodiments, the fastener can be any suitable coupling mechanism, such as a male/female fastener, a button, Velcro, a magnetic strip or a string. The second end portion 364 of the second strap 360 is coupled to the external frame 310 via fastener 382. Fastener 382 can be similar to fastener 359.

The third strap 370 includes a first end portion 372 and a second end portion 374. As described above, the first end portion 372 is configured to be coupled to the second end portion 354 of the first strap 352 via fastener 358. In some embodiments, the fastener 358 is a snap connector that allows the third strap 370 to rotationally pivot with respect to the first strap 352. In other embodiments, the fastener can be any suitable coupling mechanism, such as a male/female fastener, a button, Velcro, a magnetic strip or a string. The second end portion 374 of the third strap 370 is coupled to the external frame 310 via fastener 385. Fastener 385 can be similar to fastener 358. The second strap 360 and the third strap 370 are configured to hold the bottom portion of the external mask 310 against the user's eye region.

In the first configuration (FIG. 14), the first strap 352 is positioned at the eye level of the user. Accordingly, when the first strap 352 is placed around the user's head to hold the external frame (along with the gel pack and/or the sheet) against the eye region of the user, an amount of pressure is applied to the eye region of the user, including an amount of pressure on the eyes of the user. In the second configuration (FIG. 15), the first strap 352 is positioned above the eye level of the user. This causes the portion of the external frame 310 between the fastener 380 and the fastener 382, and the portion of the external frame 310 between the fastener 383 and the fastener 385 to be pulled away from the user's eye region when the first strap 352 is placed around the user's head to hold the external frame (along with the gel pack and/or the sheet) against the eye region of the user. Said another way, a bend is created in the portion of the external frame 310 between the fastener 380 and the fastener 382, and the portion of the external frame 310 between the fastener 383 and the fastener 385. This can be seen in FIG. 16. This causes a pressure that is less than the pressure applied to the eyes of the user in the first configuration to be applied to the eyes of the user, while more pressure is applied to the regions above and below the eyes of the user (e.g., the periphery of the user's eye region). Accordingly, the embodiment shown and described in FIGS. 14-16 allows a user to decrease the amount of pressure applied to their eyes by varying the location of the straps.

While shown in FIGS. 14-16 as having two positions, in other embodiments, the first strap can have any number of positions on the external frame. In some embodiments, for example, the external frame can define a toothed opening configured to receive an adjustment projection of the strap. The adjustment projection can be configured to slide within the toothed opening, allowing the strap to be positioned at various points on the external frame (e.g., at points between the snaps 380 and 381, and 383 and 384). Teeth within the toothed portion are configured to maintain the adjustment projection at a position selected by the user. In other embodiments, any other type of suitable adjustment mechanism can be used. This allows the user to vary the pressure applied to their eyes with greater resolution.

While shown in FIGS. 14-16 as a single monolithically formed strap, in other embodiments, the first strap has two or more separable portions that can be coupled together by using releasable coupling mechanisms such as Velcro, male/female snap connectors, a buckle, and/or the like. Such strap portions can be adjusted using Velcro, a buckle, and/or any other suitable adjustment mechanism.

In still other embodiments, the first strap, the second strap and the third strap can be monolithically formed. In such an embodiment, the end portions of the monolithically formed strap can be "v" shaped such that the strap can be coupled to both sides of the external frame at two positions. In yet other embodiments, a single strap can be used that is coupled to two "v" shaped connectors at the end portions of the single strap. The "v" shaped connectors can be coupled to the external frame at two positions on both sides of the external frame.

While shown and described in FIGS. 14-16 as being coupled to the external frame, in embodiments where an external frame is not used, the straps can be coupled directly to the gel pack. In other embodiments, the straps are not coupled to the frame or the gel pack but wrap around the outside of the gel pack and hold the gel pack against the user's eye region by friction. Said another way, the gel pack is sandwiched between the straps and the user's eye region. In such an embodiment, the straps can be adjustably positioned on the outside of the gel pack such that a desired pressure is exerted on the user's eye region.

In still other embodiments, the straps can be coupled to an intermediate member that is then coupled to the gel pack. In some embodiments, for example, the straps are coupled to an edge support member. In other embodiments, the straps are coupled to a plastic cover that can be coupled to the gel pack and/or hold the gel pack in place by friction. In yet other embodiments, the intermediate member can be a piece of "Y" or "T" shaped plastic. In such embodiments, a strap can be coupled to a first end portion of the plastic and the other two end portions of the plastic are coupled to the gel pack. In other embodiments, the piece of "Y" or "T" shaped plastic guides a "v" shaped portion of the strap (or alternatively separate straps that form a "v" shape) to the gel pack. In such embodiments, the strap is coupled to the gel pack and the piece of "Y" or "T" shaped plastic provides the strap with increased stiffness.

In some embodiments, the external frame is constructed with an arc-shaped permanent bend similar to the bend achieved when the strap system 350 of FIGS. 14-16 is in the second configuration. Said another way, in such embodiments, the external frame has a bend similar to the bend shown in FIG. 16 when in a resting position (e.g., similar to the bend between the fastener 380 and the fastener 382, and the bend between the fastener 383 and the fastener 385 in FIG. 16). Said yet another way, in such embodiments, the external frame is biased to return to its position with an arc-shaped bend after it has been flexed. In such embodiments, when the first strap is positioned at the eye level of the user, a substantially similar pressure as that achieved when the strap system 350 of FIGS. 14-16 is in the second configuration, is applied to the eye region of the user. Accordingly, an even lower pressure can be achieved if the first strap is placed above the eye level of the user on a frame having a permanent bend. Depending on how much the frame is bent, and the stiffness of the bend in the frame, the pressure applied can be decreased further. Thus, a user can vary the pressure applied to the eye region based on the positioning of the straps, the amount of bend in the frame, or both.

Having an external frame with an arc-shaped permanent bend also allows a gel pack with a greater volume to be used, thus increasing the duration of the thermal treatment. Having a greater volume of the gel pack provides a greater pressure applied on the eye region of the user. By first having a lower pressure applied by the frame (using a frame with an arc-shaped permanent bend and/or straps coupled to the frame above eye level), a gel pack having a greater volume can be used without providing the greater pressure that would be produced from a flat frame with eye level straps.

In other embodiments, separate arc-shaped members can be removably coupled to the external frame to define the arc-shaped bend. For example, in some embodiments, a stiff piece of material having a bend can be coupled to each side of the frame. The stiff piece of material can be coupled using any suitable coupling mechanism, such as, for example, a snap, a clip, and/or the like. In such an embodiment, a user can decide whether to have the arc-shaped bend in the frame or not by attaching the stiff piece of material to the frame or leaving it off the frame. In still other embodiments, the arc-shaped members can be bendable by the user such that the user can determine and adjust the amount of bend in the frame.

Figure 17:
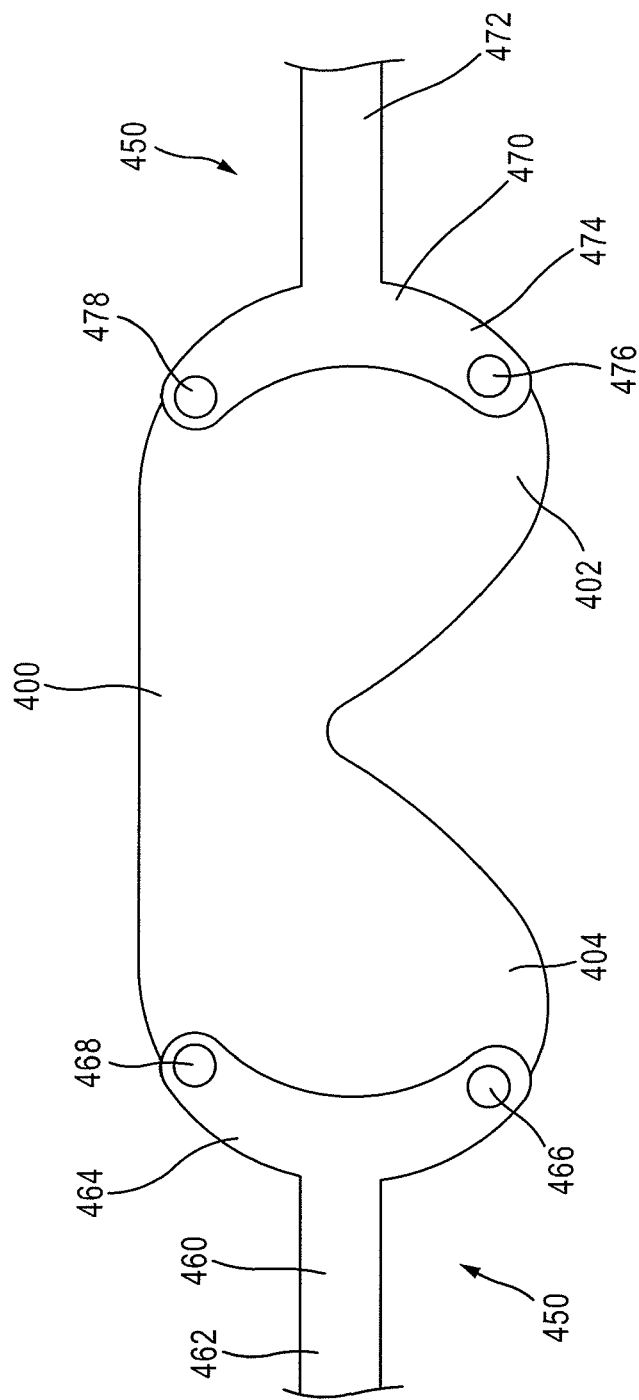
FIG. 17 is a front view of a gel pack attached to a multi-part frame, according to another embodiment.

FIG. 17 shows a front view of a gel pack 400 coupled to a multi-part frame 450, according to another embodiment. The gel pack 400 has a left portion 402 and a right portion 404, and is functionally and structurally similar to the other gel packs shown and described herein. The left portion 402 is configured to be coupled to a first portion 470 of the multi-part frame 450, and the right portion 404 is configured to be coupled to a second portion 460 of the multi-part frame 450. In some embodiments, the outer edge of the gel pack includes an edge support member configured to help support at least a portion of the weight of the gel pack such that the gel pack does not buckle when the gel pack is in a vertical position secured against the eye region of the user.

The first portion 470 of the multi-part frame 450 includes a strap 472 and a retention portion 474. The retention portion 474 has a first fastener 476 and a second fastener 478. The fasteners 476, 478 are configured to attach the first portion 470 of the multi-part frame 450 to the gel pack 400. In some embodiments, the fasteners 476, 478 are snap connectors configured to releasably couple the first portion 470 of the multi-part frame 450 to the left portion 402 of the gel pack 400. In other embodiments, the fasteners can be any suitable coupling mechanisms, such as a male/female fastener, a button, Velcro, a magnetic strip or a string. In other embodiments, the first portion of the multi-part frame can be permanently coupled to the gel pack by any suitable means, such as, for example, glue, grommets, and/or the like.

The strap 472 is configured to wrap around the head of a user and coupled to the strap 462 of the second portion 460. The strap 472 can be coupled to the strap 462 by any suitable means. In some embodiments, the strap 472 and the strap 462 can be collectively adjusted such that the multi-part frame can fit various head sizes. In other embodiments, the strap 472 is monolithically formed with the strap 462 (e.g., forming a single strap).

Similarly, the second portion 460 of the multi-part frame 450 includes a strap 462 and a retention portion 464. The retention portion 464 has a first fastener 466 and a second fastener 468. The fasteners 466, 468 are configured to attach the second portion 460 of the multi-part frame 450 to the gel pack 400. The fasteners 466, 468 are structurally and functionally similar to the fasteners 476, 478.

Figure 18:
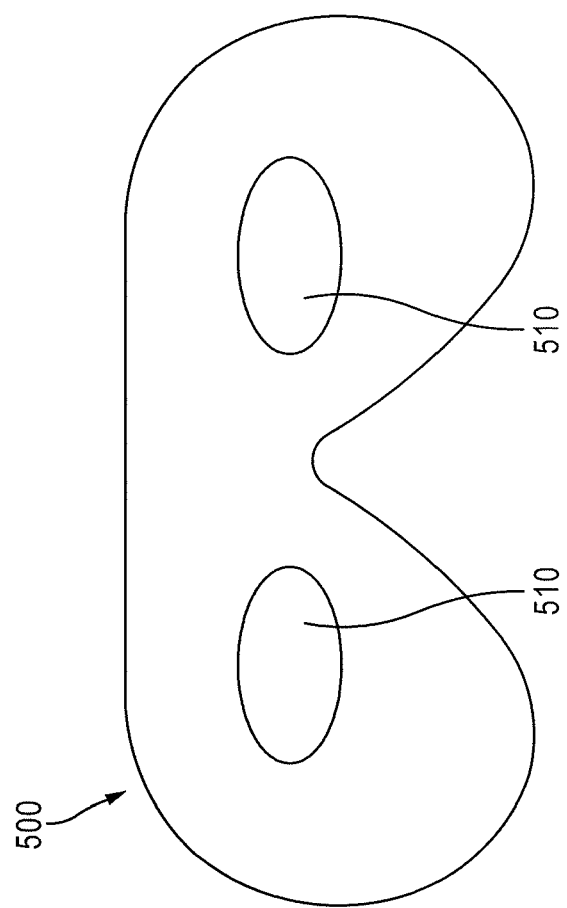
FIG. 18 is a front view of a heat shield, according to another embodiment.

FIG. 18 is a front view of a heat shield 500, according to another embodiment. The heat shield 500 defines two apertures 510. The heat shield 500 is configured to be placed between a gel pack and the eye region of a user and is configured to reduce the amount of thermal energy from the gel pack felt by the user in certain areas (by thermal energy it is meant that hot or cold energy can be felt by the user from the presence of the gel pack). Specifically, the heat shield 500 allows a greater amount of thermal energy to contact the portion of the user's body that is aligned with the apertures 510 than contacts the rest of the body disposed against the heat shield 500. Said another way, the heat shield 500 allows a greater amount of thermal energy to be felt by the user at the eye region and restricts the amount of heat felt by the user at the body regions surrounding the eye region.

The heat shield 500 can be constructed of any material configured to block the thermal energy of the gel pack. In some embodiments, for example, the heat shield 500 can be constructed of a nylon fabric.

In some embodiments, a non-woven sheet can be placed between the heat shield 500 and the user's eye region, as described above. In other embodiments, small eye pads fabricated from a material similar to the sheet can be placed in the apertures of the heat shield instead of using a full sheet.

While shown and described as being coupled to the external frame, in embodiments where an external frame is not used, the heat shield can be coupled directly to the gel pack.

In some embodiments, an eye cover can be coupled to the gel pack and/or an external frame to block light from reaching the user's eye region. The eye cover can be similar to the heat shield 500 without the apertures 510 and can be constructed of any material configured to block light penetration, such as, for example, a nylon fabric or a thin sheet of plastic.

The heat shield 500 and/or the eye cover can be releasably or permanently attached to a gel pack and/or a frame by any suitable means, such as, for example, male/female fasteners, buttons, Velcro, magnetic strips, strings, snaps and/or glue. In other embodiments, the heat shield and/or the eye cover is not attached to a frame or a gel pack and is instead held in place by being pressed between the gel pack and/or the frame and the user's body.

Referring to FIG. 12, in certain embodiments, external frame 164 further comprises a bridging portion 119 that bridges the top portion (both left and right top portions 148 and 152) and the bottom portion (both left and right bottom portions 154 and 156). In this embodiment, external frame comprises a left section 107 whose internal periphery 111 defines a left relief opening 113 and a right section 109 whose internal periphery 115 defines a right relief opening 117. The relief openings are sized to allow a user to directly manipulate the position of the gelatinous substance in the gel mask by applying topical pressure to the gelatinous substance, a feature that is useful when the overall compressive tension in the frame is kept low but the user wants to selectively increase the compress effect in certain areas. Such relief openings also reduce some of the compressive pressure that would come from increasing the backwards tension on the frame. For instance, the relief openings allow the frame to focus such pressure on the periphery of the targeted body area rather than on the center of that area. The relief openings can have any suitable shape such as tear-shaped or circular, for example.

The relief openings can be directly exposed to the atmosphere or can be covered with a thin layer of fabric, plastic, foil, or other material which would cover the gel pack underlying the openings but would be flexible enough to allow the user easily to manipulate the gel. Certain materials can be selected to insulate the gel pack by reducing the amount of convective heat exchange with the surrounding air.

Figure 13:
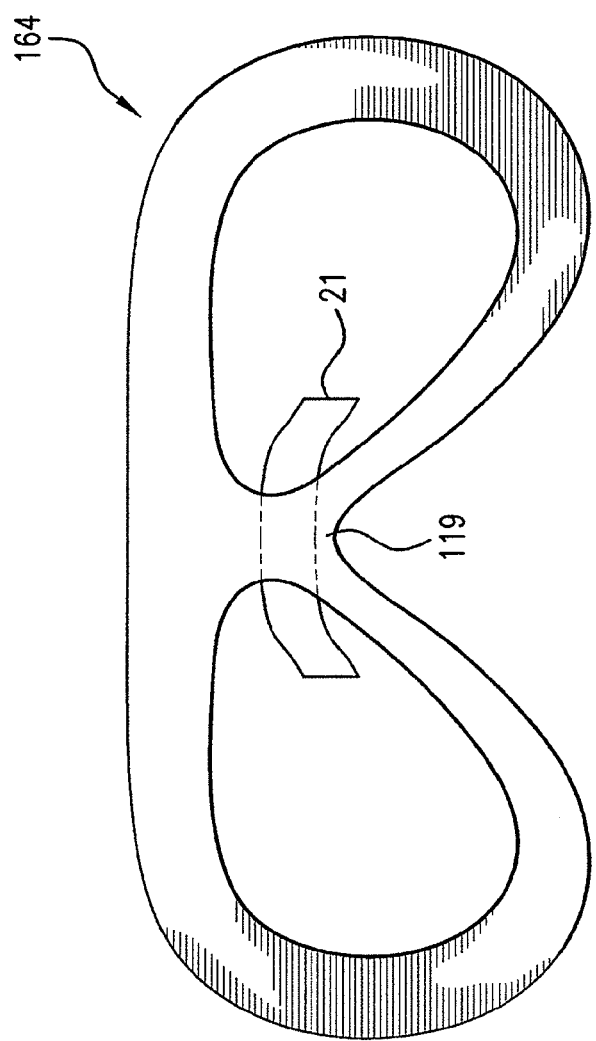
FIG. 13 is a front view of an external frame and gel impresser according to another embodiment.

In reference to FIG. 13, in certain embodiments, an eye compress assembly further comprises a gel impressor 21, which is a flexible bendible strip that can be placed in contact with the back surface of bridging portion 119 (i.e. the surface that is configured to be in contact with the gel pack). Gel impressor 21 can provide a hands-free option for creating selected indentation in certain areas of the gelatinous substance of the gel pack. Some users who use towels for wet compress therapy have noted a desire to keep mild pressure in the specific area of the nasal corners of each eye (the areas overlying the nasal canthi) in order to provide extra comfort and relief of symptoms. Gel impressor 21 provides a way for users to apply such directed therapy at these locations. In some embodiments, the gel impressor 21 is made of a flexible and bendable material that retains the shape to which it is bent. Soft metals such as aluminum are one example. In other embodiments, the gel impressor is made of plastic and or any other material that can press the gel pack against the nasal corners of each eye.

In some embodiments, a gel impressor is made from a piece of sheet aluminum of approximately 0.020 gauge thickness, approximately 2½" wide by ½" high. This impressor is placed on the back surface of the bridging portion of the external frame in a horizontal configuration (such that the width of the impressor is in the horizontal plane). The user is then free to squeeze the two ends of the impressor back toward the nasal canthi in a very natural manner (similar to pinching the bridge of the nose between the thumb and forefinger). This achieves a desired targeted effect of having the ends of the impressor continue to press the gelatinous substance of the gel pack in toward the nasal canthi, and the user can thereupon continue to experience the therapeutic benefit of the eye compress assembly in a hands-free manner. While the illustrated gel impressor is positioned to apply pressure over the nasal canthal regions, an impressor can be repositioned and applied to other anatomic regions as well.

In some embodiments, the external frame can be manufactured with a material that is stiff enough to support at least a portion of the gravitational weight of the gel pack, but bendable enough to serve its intended function. Said another way, when an external frame, sized and shaped for anatomic use in a particular area, including optional relief openings, is placed vertically upright and a gel pack that is also designed for such anatomic use is attached to the external frame, the external frame can be stiff enough to resist buckling or bending, thereby supporting the gel pack's weight and maintaining its shape. However, when the external frame is bent over a body part, such as when the external frame is bent to drape over the nasal bridge, the external frame can exhibit flexibility so as to conform to some degree with the external contour of the body part (such as the face), rather than remaining in a stiff, flat, and unbent configuration. This flexibility can be of a sufficient degree that, when the frame is subjected to forces provided by the materials mentioned above as possible contents of the strap, the frame will bend over the body part and thereby press against the underlying gel pack along the full extent (height and length) of the underlying gel pack. A flexible material may also allow the frame to be folded easily in half, down its central midline, a feature which would allow convenient insertion into a case that would be sized and shaped for the express purpose of containing the external support for travel and/or storage. In some embodiments, the frame is constructed of a microwavable material. In other embodiments, the frame is constructed of a non-microwavable material. In some embodiments, a waterproof material is use because of the expected use of wet sheets as part of compress therapy, although the wet sheets would not tend to come into direct contact with the external frame during routine use.

With respect to specific materials from which the external frame can be fabricated, any one of a variety of plastics may be suitable including, but not limited to, polymers such as polyethylene, polypropylene, polycarbonate, polymethyl methacrylate, polyethylene terephthalate, co-polymers thereof, and combinations thereof. Polypropylene (as well as other plastics) are easily dyed to different colors, a factor that can allow easy and unique identification of external support among different users in a household. Additional materials that may be used include stiffened foams, cardboard or similar paper materials, self-welted and/or stiffened fabrics, and the like. If permanently attached to the gel pack or in other circumstances where the external frame is heated with the gel pack, the material of the external frame can show no significant degradation under repeated exposure to microwave radiation. The definition of "significant degradation" is the same in this context as described above with respect to a gel pack. In experimentation, a 0.030" (30 gauge) sheet of polypropylene, die-cut to the design shown in FIG. 12 was found to be lightweight and comfortable in use, resistant to sagging or stretching, readily bendable over the nasal bridge, and resistant to multiple (greater than 50) exposures to heat and to microwave irradiation.

In certain embodiments, an external frame is covered or layered with a fabric or other soft or flexible material to provide a softer external surface, in order to improve user comfort when handling the external frame.

The external frame can be designed to support and maintain the soft gel pack and/or sheet in position against the body, without the need to forcibly strap or compress these elements into position in order to keep them in place. The adjustment of the intensity of compression of the gel pack can be achieved through means (such as via a strap) that are largely independent from the support functions of the external frame.

The below exemplary description of an exemplary eye compress assembly illustrates these principles. First, the support action of the external frame will be explained. When the user of an eye compress assembly, such as that shown in FIG. 11, for example, is in an upright position, the top portion of gel pack 20 is affixed to the top portion of external frame 164. The frame itself is made of a material that does not sag when supporting the weight of the gel, so that the top portion of frame 164 maintains the top portion of gel pack 20 at a specified height in relation to the anatomy. The bottom portion of frame 164 may be designed so that it does not touch the user's skin directly, but is instead cushioned by the lower border of the bottom portion of the gel pack, while the top portion of external frame 164 maintains the support of the top portion of gel pack 20.

Next, the compressive action of the frame will be explained. When the user of the illustrated eye compress assembly is in an upright position and the strap is placed around the head with minimal tension, the strap may be loose enough so that no compressive force is transmitted to the user's face. In this case, the bottom portion of the external frame rests upon the upper portion of the cheek, and the upper portion of the frame is tilted away from the eyes, so that the gel pack and/or the sheet remains in front of the eyes but without necessarily coming into direct contact with the eyelids or periorbita. When the user desires to increase the compressive intensity of the compress assembly, the user adjusts the strap in order to increase tension in the strap, possibly by using a buckle or other type of strap-adjusting mechanism. Under tension, the ends of the strap pull back against both the left and right side of the external frame creating a backwards tension on the frame that is transmitted onto gel pack and/or sheet, thus pressing the gel pack and/or sheet inwardly against the user's face.

In this exemplary description, the fasteners that keep the gel pack in a vertical orientation are kept in one area of the frame (in the eye compress assembly example, this is at the top portion of the frame), whereas the strap allowing adjustable transmission of tension, and the generation of a compressive force, are kept at another area of the frame (in this example, at both side edges of the external frame). In this exemplary description, the support for the proper positioning of the gel pack and/or the sheet in relation to the eyes comes from the vertical transmission of their weight onto the relatively stiff frame element. In contrast, the compressive effect that the external frame exerts against the gel pack and/or the sheet comes from the horizontal transmission of tension, which is effected by the surface area of the frame.

In use, the user is free to manipulate the gel pack so as to conform to the user's particular anatomy, which allows the user to more conveniently and directly manipulate the gel and achieve anatomic conformation. Once the gel is manipulated into the desired conformation, the user may again adjust the compressive force of the frame by modifying the tension in the head strap. After use, the sheet can be disposed or can be used to clean or wipe the user's face and then disposed.

The compress devices, assemblies, kits and methods can be used for a variety of conditions and purposes. In the example of ocular discomfort, hot compress assembly can be used for various eye conditions including certain types of dry eye syndrome such as, for example, meibomian gland disease and other forms of blepharitis; "styes" (hordeola and chalazia); orbital and preseptal cellulitis; acute dacryocystitis; and other conditions. Hot compresses to the eyelids and periorbita can also used for certain postsurgical states, for the promotion of feelings of relaxation, for certain cosmetic or dermatological treatments, and for various other reasons. Cold or cool compress assemblies can be used for postoperative states following periorbital, intraorbital, or eyelid surgery; for symptomatic relief of irritating conditions such as acute allergic or viral conjunctivitis; for relief of migraines; to promote feelings of relaxation; to allow the application of topical skin therapies for cosmetic and dermatologic treatments, and for various other reasons.

Examples 1-3 illustrate the performance of various types of sheets used in thermal compress therapy. Example 4 illustrates a method to improve microwave heating of a gel pack.

EXAMPLES

Example 1

The Following Example Compares the Thermal Conductivity Effects of Dry and Wet Non-Woven Sheets 1.A. Comparison of Single Layer Wet and Dry Non-Woven Sheets.

Figure 19:
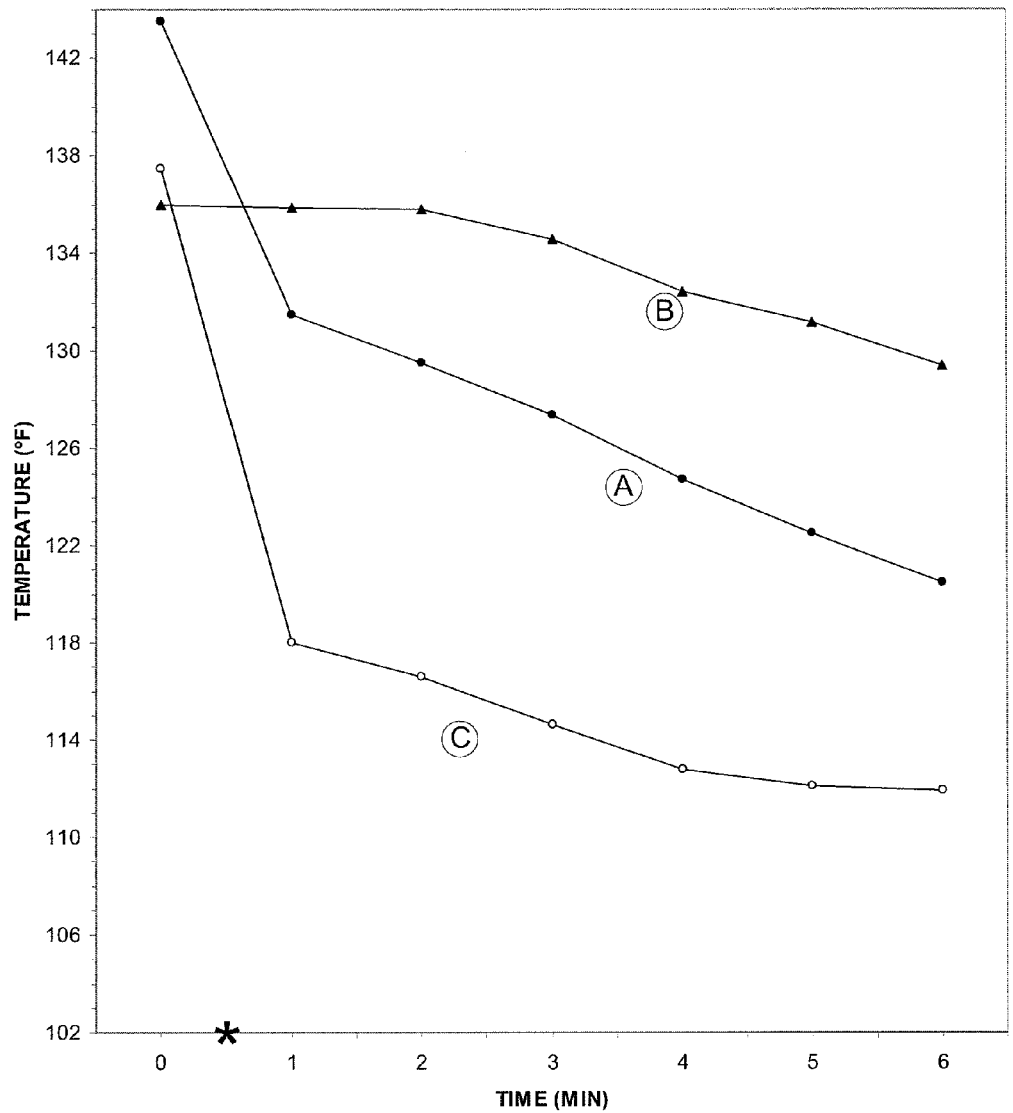
FIG. 19 is a graph of the temperature of a gel pack over time using a wet non-woven sheet and a dry non-woven sheet.

A single gel pack was heated in a microwave oven. Three thermometers were placed in contact with three different areas of the gel pack surface. Maximum stable temperatures were recorded. Thirty seconds later, one of three interventions was made:
A: "Wet NW"=A wet non-woven sheet was placed under the thermometer tip.
B: Nothing was done (control).
C: "Dry NW"=A dry non-woven sheet was placed under the thermometer tip.
The temperature of each thermometer was then recorded at one-minute intervals. All temperatures are in ° F. The results are shown in FIG. 19 and Table 1. It should be noted that the asterisk in FIG. 19 indicates when the dry non-woven sheet or wet non-woven sheet was applied to the gel pack.

TABLE 1

|  | A* | B* | C* |
|---|---|---|---|
|  | 143.5 | 136.0 | 137.5 |
| 0.50 min | Wet NW | (Nothing) | Dry NW |
| 1.00 min | 131.5 | 135.9 | 118.0 |
| 2.00 min | 129.5 | 135.8 | 116.6 |
| 3.00 min | 127.4 | 134.6 | 114.6 |
| 4.00 min | 124.7 | 132.4 | 112.8 |
| 5.00 min | 122.5 | 131.2 | 112.1 |
| 6.00 min | 120.5 | 129.4 | 111.9 |
| Initial drop in temperature: | 12.0 | 0.1 | 19.5 |
| Subsequent drop: | 11.0 | 6.5 | 6.1 |
| Total drop: | 22.0 | 6.6 | 25.6 |

This experiment shows that, while a wet non-woven sheet provides some thermal barrier effect, it also allows more heat conductivity than a dry non-woven sheet.

The wet sheet did undergo a more rapid decline in temperature relative to the dry sheet, probably because of evaporation. Because, during actual use, the sheet will be in contact with the skin of the user, such evaporative heat loss will be directed into the user's skin, and benefit the user.

1.B. Comparison of Layered Dry and Wet Sheets

Gel packs were heated in a microwave oven, and surface temperatures were recorded. Sheets were placed on top of the gel pack, and temperatures were then recorded from the most superficial layer present. Two experimental protocols were followed.

1.B.i. In the first protocol, a dry sheet was placed over the gel pack; and then a wet sheet was interposed between the gel pack and the dry sheet. Results are shown in Table 2.

TABLE 2

|  | Trial#: | | |
|---|---|---|---|
| Protocol 1.B.i. | 1 | 2 | 3 |
| Gel pack only | 142 | 140 | 144 |
| Gel pack + dry sheet | 121 | 121 | 122 |
| Gel pack + Wet sheet + Dry sheet* | 127 | 126 | 128 |

*The temperature first dipped, but then rose; the values shown are the maximum temperature following the rise.

1.B.ii. In the second protocol, a wet sheet was placed against the gel pack, and a dry sheet was placed on top of the wet sheet. The dry sheet was then removed; finally, the wet sheet was then removed. Results are shown in Table 3.

TABLE 3

|  | Trial#: | | | |
|---|---|---|---|---|
| Protocol 1.B.ii. | 1 | 2 | 3 | 4 |
| Gel pack only | 144 | 144 | 122 | 145 |
| Gel pack + Wet sheet + Dry sheet* | 131 | 128 | 115 | 130 |
| Gel pack + Wet sheet | 134 | 132 | 118 | 133 |
| Gel pack only | 128 | 125 | 116 | 126 |

*The temperature first dipped and then rose; the values shown are the maximum temperature following the rise.

Tables 2 and 3 show that the heat conductivity effect of a wet sheet is superior to that of a dry sheet. This is an unexpected result, given previous teaching in the art directly away from this conclusion. Tables 2 and 3 also show that placing a dry sheet or dry layer between the gel pack and a wet sheet will decrease the thermal conductivity to the user's face.

1.C. Subjective Comparison of Dry Vs. Wet Non-Woven Sheets.

An eye mask shaped gel pack was heated using microwave activation, to a temperature of around 125 to 135° F. Under experimental conditions, a kit having the heated gel pack and a dry non-woven sheet shaped was applied to a user in the manner illustrated in FIG. 11. The kit was removed from the user's face, a wet sponge was touched to the dry non-woven sheet in order to moderately dampen its surface, and the kit was replaced on the user's face.

RESULTS: With the dry non-woven sheet in place, the user did not appreciate the thermal effect desirable in a hot ocular compress. Once the non-woven sheet was dampened and the kit was reapplied, the user immediately appreciated an improved thermal effect that exceeded the degree of significance suggested by the objective temperature recordings made in other experiments.

Example 2

The Following Example Compares the Use of Non-Woven Fabric Sheets with Paper Towels Under 5 Conditions (2.A-2.E).

The non-woven sheets used were made of polymer and pulp, as previously described. Bounty® two-ply White paper towels were also used. Sheets were either cut to the size and contour shown in the illustrated embodiment of FIG. 8, or cut to smaller sizes as needed.

2.A. Pre-Moistening Test

To simulate the preparation of a pre-moistened sheet, all sheets were immersed in a shallow water bath and then removed after 10 minutes. Unexpectedly, the 2-ply paper towel sheets come apart into single plies. This separation occurred as little as 15 seconds after immersion.

This illustrates that long-term preparation of a pre-moistened two-ply paper towel sheet is impractical and unreliable.

2.B. Water Absorption Test.

3 ml (3.0 g) of water was placed in the center of a scale. Sheets of various sizes and materials were used to absorb the water from the scale until saturated. Each sheet was then held up by one corner and allowed to drip gently onto the scale (splashing was avoided) until the time between the drips exceeded 5 seconds. The residual weight of the water remaining on the scale was then recorded. The weight of absorbed water in the sheet was calculated by subtracting the residual weight of water on the scale from the initial weight of the water (3.0 g). The water capacity per square inch of each sheet type was then calculated. The potential water capacity of a full eye compress sheet (around 26.9 square inches) was then calculated. Results are shown in Table 4.

TABLE 4

| | Sheet Material | | |
|---|---|---|---|
| | Non-woven 1-Ply 2" × 3" | Paper Towel 2-Ply 3" × 3" | Paper Towel 1-Ply 3" × 3" |
| Trial# | Weight of Water Left on Scale ("Residual"), (g) | | |
| 1 | 0.3 | 0.5 | 2.2 |
| 2 | 0.3 | 0.5 | 2.3 |
| 3 | 0.3 | 0.5 | 2.3 |
| 4 | 0.3 | 0.5 | 2.2 |
| Avg residual wt: | 0.3 | 0.5 | 2.25 |
| Water capacity of sheet*: | 2.7 | 2.5 | 0.75 |
| Sheet, # Sq in. | 6 | 9 | 9 |
| Capacity of sheet (g/sq in): | 0.45 | 0.28 | 0.08 |
| Capacity of larger sheet (g)**: | 12.11 | 7.47 | 2.24 |

*Capacity = initial weight of water (3 g), less residual weight.
**26.9 sq inches is the area of an exemplary facial sheet This showed that a non-woven sheet can hold over 5 times as much moisture as a 1-ply paper towel, and around 60% more moisture than a 2-ply paper towel. This was an unexpected result, given that paper towels are marketed as having superior absorbency to clean up spills, whereas non-woven sheets are primarily marketed as being good for cleaning dirt from skin and other surfaces.

2.C. Drying Time Test (Using Diameter Measurement)

Drying time of different sheet materials was then tested. Three drops of water were placed on a 3"×3" sheet of different materials. The diameter of the wet or damp area was measured at successive time periods.

The drops placed on the paper towel sheet rapidly absorbed into the sheet, expanding the diameter of the wet area. Drops placed on the non-woven sheet tended to bead up and were more slowly absorbed into the sheet. The results are shown in Table 5.

TABLE 5

| | Diameter of Moist Area, in Inches, on 3" × 3" sheet material | | |
|---|---|---|---|
| # mins | Non-woven 1-ply | Paper Towel 2-ply | Paper Towel 1-ply |
| 0 | 0.625 | 1.625 | 1.5 |
| 5 | 0.625 | 2.25 | 2.5 |
| 10 | 0.625 | 2.25 | 2.25 (very faint) |
| 15 | 0.625 | 2.0 (faint) | Dry |
| 20 | 0.625 | 2.0 (very faint) | |
| 25 | 0.75 | 1.5 (very faint) | |
| 30 | 0.75 | Dry | |
| 60 | 1 × 1 (still damp) | | |

This experiment showed that a 1-ply non-woven sheet can retain moisture twice as long as a 2-ply paper towel sheet and 4 times as long as a 1-ply paper towel sheet. This was an unexpected result, as explained above.

2.D. Drying Time Test (Weight-Based, During Actual Experimental Use)

The drying time of a two-ply paper towel sheet was compared to that of a single-ply non-woven fabric sheet during actual use on a human subject in the context of using a full eye compress assembly.

This experiment was performed using full-size sheets (one non-woven, one paper towel) shaped as in FIG. 8. Dry weights were taken. The sheets were moistened using a spray bottle filled with tap water. Wet weights were taken. The sheets were applied to gel packs of 2.5 ounces which had been heated in a microwave oven and manipulated to achieve even homogeneous temperatures, and the gel pack-and-sheet assemblies were then applied to the face of a user, in the manner shown in FIG. 11. The temperature between the user's skin and the sheet was measured at the start and at the end of a 5-minute period. The final weights of the sheets were then taken. Moisture loss was calculated. The results are shown in Table 6.

TABLE 6

| Sheet Type | Non-woven | Paper Towel (2-ply) |
|---|---|---|
| Dry Weight (oz.) | 0.06 | 0.05 |
| Starting Wet Weight (oz.) | 0.21 | 0.16 |
| Skin-Sheet Temp, at start, ° F. | 115 | 110 |
| Skin-Sheet Temp, after 5 mins, ° F. | 103 | 98 |
| Ending Wet Weight (oz.) | 0.18 | 0.11 |
| Weight Loss due to Evaporation (oz.) | 0.03 | 0.05 |
| Initial Weight of Water (calculated, oz.) | 0.15 | 0.11 |
| Percent Water Loss | 20% | 45% |

This experiment shows that, under experimental hot compress use on the human body, the percentage of water lost from the non-woven sheet was less than half the percentage of water lost from the paper towel, even though the skin-sheet temperature was maintained at 5 degrees higher for the non-woven sheet than for the paper towel sheet. This was an unexpected result, as explained above.

2.E. The Wear-and-Tear Test

Buttonholes 0.625" in width were cut into the sheets. The sheets were buttoned and unbuttoned 10 times onto a rubber button. The results are shown in Table 7.

TABLE 7

| Sheet Type | Buttonhole widths after 10 buttonings |
|---|---|
| Non-woven, Dry | 0.625" and 0.625" |
| Non-woven, Wet | 0.625" and 0.625" |
| 1-Ply Paper Towel, Dry | 0.625" and 0.750" |
| 1-Ply Paper Towel, Wet | One buttonhole tore open completely (through the top of the sheet). The other buttonhole tore open to 1.5" |

This test demonstrated the inferiority of a single-ply paper towel to manipulation in an embodiment where a wet sheet is attached to an external frame via buttons. By extension, the durability of paper towels to other manipulations would presumably be worse than the durability of non-woven sheets.

Example 3

Thermal Effects of Non-Woven Fabric Sheets and Terrycloth Towels

Figure 20:
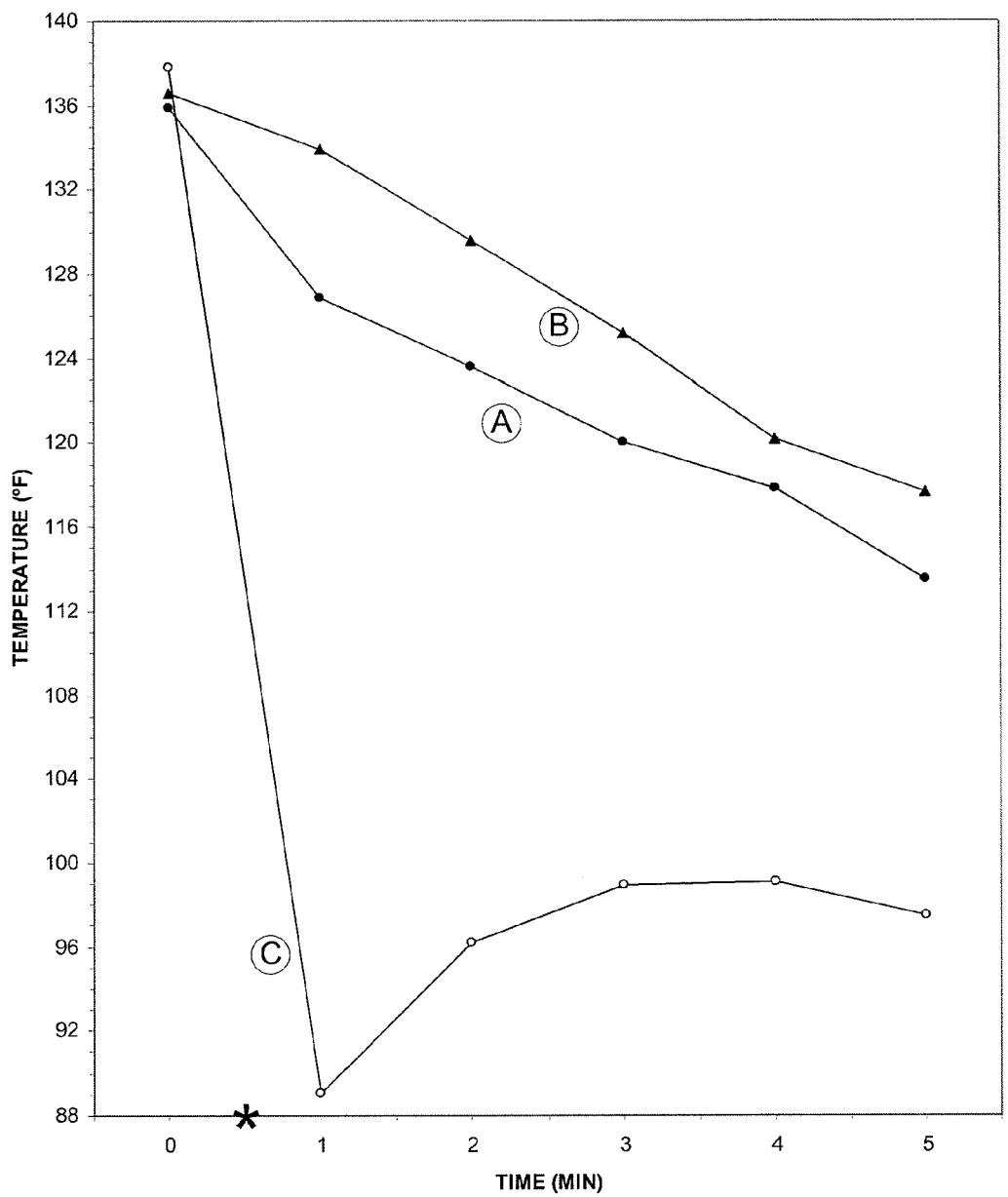
FIG. 20 is a graph of the temperature of a gel pack over time using a wet non-woven sheet and a wet terrycloth towel.

In this experiment, a single gel pack was heated with microwave activation. Maximum stable temperatures on each of three different areas on the surface of the gel pack (each less than 1" from the next area) were measured using three different thermometers. Various interventions were made as follows:
A: "Wet NW"=A wet non-woven sheet was placed under the thermometer tip
B: Nothing was done (control)
C: "Wet TC"=A wet terrycloth towel was placed under the thermometer tip
The temperature was then recorded at one-minute intervals. All temperatures are in ° F. FIG. 20 and Table 8 show the results. It should be noted that the asterisk in FIG. 20 indicates when the wet non-woven sheet or terrycloth towel was applied to the gel pack.

TABLE 8

|  | A | B | C |
|---|---|---|---|
| Start | 135.9 | 136.6 | 137.8 |
| 0.50 min | Wet NW* | (Nothing) | Wet TC* |
| 1.00 min | 126.9 | 133.9 | 89.1 |
| 2.00 min | 123.6 | 129.6 | 96.2 |
| 3.00 min | 120.0 | 125.2 | 98.9 |
| 4.00 min | 117.8 | 120.2 | 99.1 |
| 5.00 min | 113.5 | 117.7 | 97.5 |
| Initial drop in temperature: | 9.0 | 2.7 | 48.7 |
| Subsequent drop: | 13.4 | 16.2 | (8.4) |
| Total drop: | 22.4 | 18.9 | 40.3 |

This experiment illustrated that the initial very large drop in temperature caused by the thermal barrier effect of the wet terrycloth towel was sustained through time. Even though the initial temperature of the gel pack was quite hot (nearly 140° F.), the wet terrycloth towel blocked heat so significantly that the effective temperature at the surface of the terrycloth towel never reached the preferred minimum therapeutic window of 104° F., much less the estimated optimal therapeutic level of 120 to 125° F.

Example 4

How to Reduce the Incidence of Hot Spots when Microwaving an Eye Mask Shaped Gel Pack Microwave heating of eye mask shaped gel packs often produces hot and cold spots in the gel pack, which are uncomfortable to the user. To improve even heating, a method of using a thin damp sponge (approximately ½" thick, 4"×9", wet weight 2.5 ounces) laid on top of the gel pack was developed, and was compared to a conventional dry heating method.

Temperatures were measured after microwave heating, using a thermocouple, on the right and left sides of the gel pack, and the difference in temperature between the two sides of the gel pack was calculated. Results are shown in Table 9.

TABLE 9

| Differences in Temperature, in ° F. (Right and Left sides of Gel Pack) | |
|---|---|
| Sponge | No Sponge |
| 3 | 0 |
| 3 | 1 |
| 4 | 6 |
| 4 | 8 |
| 5 | 9 |
| 5 | 18 |
| 6 | 19 |
| 6 | 20 |
| 10 | 27 |
| 19 | 31 |
| Average: 6.5 | 13.9 |

This illustrates that the average inter-side difference in temperature was, on average, less for the sponge heating than for the no-sponge heating method.

The foregoing description and examples have been set forth merely to illustrate embodiments and are not intended as being limiting. Each of the disclosed aspects and embodiments may be considered individually or in combination with other aspects, embodiments, and variations. Further, while certain features of embodiments may be shown in only certain figures, such features can be incorporated into other embodiments shown in other figures. In addition, unless otherwise specified, none of the steps of the methods described are confined to any particular order of performance. Modifications of the disclosed embodiments incorporating the spirit and substance may occur to persons skilled in the art and such modifications are within the scope of the invention. Furthermore, all references cited herein are incorporated by reference in their entirety.

What is claimed is:

1. An apparatus, comprising:
an external frame having at least one attachment mechanism attachable to a gel pack, the external frame being fabricated from a material having a rigidity sufficient to support at least a portion of a gravitational weight of the gel pack such that the external frame does not buckle when the gel pack is attached to the external frame and the external frame is in a substantially vertical orientation secured against an eye region of a user;
the external frame having a top edge portion, a bottom edge portion, a left side region and a right side region, each of the left side region and the right side region having an upper portion, a central portion and a lower portion; and
a strap system including:
a first strap having a first end portion configured to be coupled to the upper portion of the left side region when the external frame is in the substantially vertical orientation secured against the eye region of the user, the first strap having a second end portion;
a second strap having a first end portion configured to be coupled to the upper portion of the right side region when the external frame is in the substantially vertical orientation secured against the eye region of the user, the second strap having a second end portion configured to be coupled to the second end portion of the first strap when the external frame is in the substantially vertical orientation secured against the eye region of the user;

a third strap having a first end portion configured to be coupled to the lower portion of the left side region, the third strap having a second end portion configured to be rotatably coupled to a point on the first strap, the third strap and a portion of the first strap from the first end portion of the first strap to the point on the first strap defining a V-shape when the external frame is in the substantially vertical orientation secured against the eye region of the user; and a fourth strap having a first end portion configured to be coupled to the lower portion of the right side region, the fourth strap having a second end portion configured to be rotatably coupled to a point on the second strap, the fourth strap and a portion of the second strap from the first end portion of the second strap to the point on the second strap defining a V-shape when the external frame is in the substantially vertical orientation secured against the eye region of the user.

2. The apparatus of claim 1, wherein the lower portion of the left side region and the lower portion of the right side region are positioned substantially below an eye level of the user when the external frame is in the substantially vertical orientation secured against the eye region of the user.

3. The apparatus of claim 1, wherein the upper portion of the left side region and the upper portion of the right side region are positioned substantially above an eye level of the user when the external frame is in the substantially vertical orientation secured against the eye region of the user.

4. The apparatus of claim 1, wherein the external frame is deformable, the central portion of the left side region and the central portion of the right side region are configured to deform convexly away from the eye region of the user when the external frame is secured against the eye region of the user and tension is applied rearwardly relative to the eye region by the first strap, the second strap, the third strap and the fourth strap.

5. The apparatus of claim 1, wherein the external frame includes a left internal periphery defining a first aperture and a right internal periphery defining a second aperture, the left internal periphery circumscribing an area substantially anterior to a left eye of the user and the right internal periphery circumscribing an area substantially anterior to a right eye of the user when the external frame is in the substantially vertical orientation secured against the eye region of the user.

6. The apparatus of claim 1, further comprising:
the gel pack, the gel pack having a single chamber, the gel pack configured to substantially cover a left eye of the user and a right eye of the user when the gel pack is attached to the external frame and the external frame is in the substantially vertical orientation secured against the eye region of the user.

7. The apparatus of claim 1, further comprising:
the gel pack, the gel pack being thermally adjustable, the gel pack configured to be in direct physical contact with a left eyelid of the user and a right eyelid of the user when the gel pack is attached to the external frame and the external frame is in the substantially vertical orientation secured against the eye region of the user.

8. The apparatus of claim 1, further comprising:
the gel pack; and
at least one moistened, disposable, fibrous, non-woven fabric sheet configured to be removably positioned between the gel pack and a left eyelid of the user and a right eyelid of the user such that the at least one sheet is in direct physical contact with the left eyelid and the right eyelid when the gel pack is attached to the external frame and the external frame is in the substantially vertical orientation secured against the eye region of the user.

9. The apparatus of claim 1, wherein the external frame has a surface area, the apparatus further comprising:
the gel pack, the gel pack being thermally adjustable, the gel pack configured to substantially cover a left eye of the user and a right eye of the user when the gel pack is attached to the external frame and the external frame is in the substantially vertical orientation secured against the eye region of the user, the gel pack having a surface area greater than the surface area of the external frame.

10. The apparatus of claim 1, further comprising:
at least one moistened, disposable, fibrous, non-woven fabric sheet configured to be removably positioned between the thermally adjustable gel pack and a left eyelid of the user and a right eyelid of the user such that the at least one sheet is in direct physical contact with the left eyelid and the right eyelid when the thermally adjustable gel pack is attached to the external frame and the external frame is in the substantially vertical orientation secured against the eye region of the user.

11. An apparatus, comprising:
a thermally adjustable gel pack;
an external frame having at least one attachment mechanism attachable to the thermally adjustable gel pack, the external frame having a surface area, the external frame being fabricated from a material having a rigidity sufficient to support at least a portion of a gravitational weight of the thermally adjustable gel pack such that the external frame does not buckle when the thermally adjustable gel pack is attached to the external frame and the external frame is in a substantially vertical orientation secured against an eye region of a user, the external frame having a top edge portion, a bottom edge portion, a left side region and a right side region, each of the left side region and the right side region having an upper portion, a central portion and a lower portion, the thermally adjustable gel pack configured to substantially cover a left eye of the user and a right eye of the user when the thermally adjustable gel pack is attached to the external frame and the external frame is in the substantially vertical orientation secured against the eye region of the user, the thermally adjustable gel pack having a surface area greater than the surface area of the external frame; and a strap system including:
a left V-shaped element extending from the left side region, the left V-shaped element having a left upper arm with a first end portion and a second end portion and a left lower arm with a first end portion and a second end portion; and a right V-shaped element extending from the right side region, the right V-shaped element having a right upper arm with a first end portion and a second end portion and a right lower arm with a first end portion and a second end portion, the first end portion of the left upper arm configured to be coupled to the upper portion of the left side region of the external frame, the first end portion of the left lower arm configured to be coupled to the lower portion of the left side region of the external frame, the second end portion of the left upper arm configured to be coupled to the second end portion of the left lower arm at a first apex, the left upper arm and the left lower arm forming a V-shape when the external frame is in the substantially vertical orientation secured against the eye region of the user, the first end portion of the right upper arm configured to be coupled to the upper portion of the right side region of the external frame, the first end portion of the right lower arm configured to be coupled to the lower portion of the right side region of the external frame, the second end portion of the right upper arm configured to be coupled to the second end portion of the right lower arm at a second apex, the right upper arm and the right lower arm forming a V-shape when the external frame is in the substantially vertical orientation secured against the eye region of the user, the upper portion of the left side region and the upper portion of the right side region are both positioned substantially above an eye level of the user when the external frame is in the substantially vertical orientation secured against the eye region of the user, the lower portion of the left side region and the lower portion of the right side region are both positioned substantially below the eye level of the user when the external frame is in the substantially vertical orientation secured against the eye region of the user.

12. The apparatus of claim 11, wherein the external frame is deformable, the central portion of the left side region and the central portion of the right side region are configured to deform convexly away from the eye region of the user when the external frame is secured against the eye region of the user and tension is applied rearwardly relative to the eye region upon the first apex and the second apex.

13. The apparatus of claim 11, wherein the external frame includes a left internal periphery defining a first aperture and a right internal periphery defining a second aperture, the left internal periphery circumscribing an area substantially anterior to the left eye of the user and the right internal periphery circumscribing an area substantially anterior to the right eye of the user when the external frame is in the substantially vertical orientation secured against the eye region of the user.

14. An apparatus, comprising:
a thermally adjustable gel pack;
an external frame having at least one attachment mechanism attachable to the thermally adjustable gel pack, the external frame having a surface area, the external frame being fabricated from a material having a rigidity sufficient to support at least a portion of a gravitational weight of the thermally adjustable gel pack such that the external frame does not buckle when the thermally adjustable gel pack is attached to the external frame and the external frame is in a substantially vertical orientation secured against an eye region of a user;
the external frame having a top edge portion, a bottom edge portion, a left side region and a right side region, each of the left side region and the right side region having an upper portion, a central portion and a lower portion, the thermally adjustable gel pack configured to substantially cover a left eye of the user and a right eye of the user when the thermally adjustable gel pack is attached to the external frame and the external frame is in the substantially vertical orientation secured against the eye region of the user, the thermally adjustable gel pack having a surface area greater than the surface area of the external frame; and
a strap system including:
a first strap having a first end portion configured to be coupled to the upper portion of the left side region when the external frame is in the substantially vertical orientation secured against the eye region of the user, the first strap having a second end portion;
a second strap having a first end portion configured to be coupled to the upper portion of the right side region when the external frame is in the substantially vertical orientation secured against the eye region of the user, the second strap having a second end portion configured to be coupled to the second end portion of the first strap when the external frame is in the substantially vertical orientation secured against the eye region of the user;
a third strap having a first end portion configured to be coupled to the lower portion of the left side region, the third strap having a second end portion configured to be coupled to a point on the first strap, the third strap and a portion of the first strap from the first end portion of the first strap to the point on the first strap defining a V-shape when the external frame is in the substantially vertical orientation secured against the eye region of the user; and
a fourth strap having a first end portion configured to be coupled to the lower portion of the right side region, the fourth strap having a second end portion configured to be coupled to a point on the second strap, the fourth strap and a portion of the second strap from the first end portion of the second strap to the point on the second strap defining a V-shape when the external frame is in the substantially vertical orientation secured against the eye region of the user.

15. The apparatus of claim 14, wherein the lower portion of the left side region and the lower portion of the right side region are positioned substantially below an eye level of the user when the external frame is in the substantially vertical orientation secured against the eye region of the user.

16. The apparatus of claim 14, wherein the upper portion of the left side region and the upper portion of the right side region are positioned substantially above an eye level of the user when the external frame is in the substantially vertical orientation secured against the eye region of the user.

17. The apparatus of claim 14, wherein the external frame is deformable, the central portion of the left side region and the central portion of the right side region are configured to deform convexly away from the eye region of the user when the external frame is secured against the eye region of the user and tension is applied rearwardly relative to the eye region by the first strap, the second strap, the third strap and the fourth strap.

18. The apparatus of claim 14, wherein the external frame includes a left internal periphery defining a first aperture and a right internal periphery defining a second aperture, the left internal periphery circumscribing an area substantially anterior to the left eye of the user and the right internal periphery circumscribing an area substantially anterior to the right eye of the user when the external frame is in the substantially vertical orientation secured against the eye region of the user.

19. The apparatus of claim 14, wherein the thermally adjustable gel pack has a single chamber.

20. The apparatus of claim 14, wherein the second end portion of the third strap is configured to be rotatably coupled to the point on the first strap and the second end portion of the fourth strap is configured to be rotatably coupled to the point on the second strap.

21. The apparatus of claim 14, further comprising:
at least one moistened, disposable, fibrous, non-woven fabric sheet configured to be removably positioned between the thermally adjustable gel pack and a left eyelid of the user and a right eyelid of the user such that the at least one sheet is in direct physical contact with the left eyelid and the right eyelid when the thermally adjustable gel pack is attached to the external frame and the external frame is in the substantially vertical orientation secured against the eye region of the user.

\* \* \* \* \*